United States Patent
Fasano

(10) Patent No.: US 7,531,504 B2
(45) Date of Patent: *May 12, 2009

(54) PHARMACEUTICAL COMPOSITION AND METHOD FOR INHIBITING GASTROINTESTINAL INFLAMMATION

(75) Inventor: Alessio Fasano, West Friendship, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 27 days.

This patent is subject to a terminal disclaimer.

(21) Appl. No.: 11/500,429

(22) Filed: Aug. 8, 2006

(65) Prior Publication Data

US 2006/0276399 A1 Dec. 7, 2006

Related U.S. Application Data

(60) Division of application No. 11/074,727, filed on Mar. 9, 2005, now Pat. No. 7,189,696, which is a division of application No. 10/648,642, filed on Aug. 27, 2003, now Pat. No. 6,936,689, which is a continuation of application No. 10/095,450, filed on Mar. 13, 2002, now Pat. No. 6,670,448, which is a division of application No. 09/127,815, filed on Aug. 3, 1998, now Pat. No. 6,458,925.

(51) Int. Cl.
*A61K 38/00* (2006.01)
*C07K 7/00* (2006.01)

(52) U.S. Cl. ............... 514/2; 514/16; 514/21; 530/300; 530/328; 424/185.1

(58) Field of Classification Search ............ 514/2, 514/12, 15, 16, 21; 530/328, 300, 324, 329, 530/350; 424/185.1
See application file for complete search history.

(56) References Cited

U.S. PATENT DOCUMENTS

| 5,945,510 | A  | 8/1999  | Fasano      |
|-----------|----|---------|-------------|
| 6,458,925 | B1 | 10/2002 | Fasano      |
| 6,506,577 | B1 | 1/2003  | Deming et al. |
| 6,670,448 | B2 | 12/2003 | Fasano      |
| 6,936,689 | B2 | 8/2005  | Fasano      |

FOREIGN PATENT DOCUMENTS

| EP | 0 557 897    |   | 9/1993  |
|----|--------------|---|---------|
| EP | 0 675 199    |   | 10/1995 |
| WO | WO 94/11505  | * | 5/1994  |
| WO | WO-94/11509  |   | 5/1994  |
| WO | WO-97/33909  |   | 9/1997  |
| WO | WO 98/37096  |   | 8/1998  |
| WO | WO-98/52415  |   | 11/1998 |

OTHER PUBLICATIONS

Bolton et al., "Loss of the tight junction proteins occludin and zonula occludens-1 from cerebral vascular endothelium during neutrophil-induced blood-brain barrier breakdown in vivo," 1998, Neuroscience, vol. 86, No. 4, pp. 1245-1257.
Jeppsson et al., "Blood-brain barrier derangement in Uremic encephalopathy," Jul. 1982, Surgery, vol. 92, No. 1, 1 page.
*Infect Immun.*, Baudry et al., 60 (2), pp. 428-434, 1992.

* cited by examiner

*Primary Examiner*—Chih-Min Kam
(74) *Attorney, Agent, or Firm*—Cooley Godward Kronish LLP

(57) ABSTRACT

Peptide antagonists of zonulin are disclosed, as well as methods for the use of the same. The peptide antagonists bind to the zonula occludens receptor, yet do not physiologically modulate the opening of mammalian tight junctions.

10 Claims, 10 Drawing Sheets

FIGURE 6

Rabbit
Intestine -   Asn Gln Arg Pro Pro Ala Gly Val Thr Ala Tyr Asp Tyr Leu Val Ile Gln
(SEQ ID NO:27)

Human Adult
Intestine -   Glu Val Gln Leu Val Glu Ser Gly Gly Xaa Leu
(SEQ ID NO:31)

Human Fetal
Intestine -   Met Leu Gln Lys Ala Glu Ser Gly Gly Val Leu Val Gln Pro Gly Xaa Ser Asn Arg Leu
(SEQ ID NO:30)

Human Adult
Heart -   Glu Val Gln Leu Val Glu Ser Gly Gly Gly Leu Val Gln Pro Gly Gly Ser Leu Arg Leu
(SEQ ID NO:28)

Human Adult
Brain -   Val Thr Phe Tyr Thr Asp Ala Val Ser
(SEQ ID NO:29)

Internal
Sequence
Human Adult
Heart -   Leu Ser Glu Val Thr Ala Val Pro Ser Leu Asn Gly Gly
(SEQ ID NO:33)

Human Adult
Brain 35 kDa
Fragment -   Xaa Xaa Asp Gly Thr Gly Lys Val Gly Asp Leu
(SEQ ID NO:32)

FIGURE 7

```
Vibrio cholerae
ZOT*                                            Phe Cys Ile │Gly Arg Leu Cys Val Gln Asp Gly│Phe Val Thr
(SEQ ID NO:38)

Human Adult
Intestine -             Glu Val Gln Leu Val Glu Ser│Gly Gly Xaa Leu
(SEQ ID NO:31)

Human Fetal
Intestine -     Met Leu Gln Lys Ala Glu Ser│Gly Gly Val Leu Val Gln Pro Gly│Xaa Ser Asn Arg Leu
(SEQ ID NO:30)

Human Adult
Heart      -             Glu Val Gln Leu Val Glu Ser│Gly Gly Gly Val Val Gln Pro Gly│Gly Ser Leu Arg Leu
(SEQ ID NO:28)

FZI/0      -                                       │Gly Gly Val Leu Val Gln Pro Gly│
(SEQ ID NO:15)

FZI/1      -                                   Val│Gly Val Leu Gly Arg Pro Gly│
(SEQ ID NO:34)

Human Fetal
Brain      -     Xaa Gly Lys Val Lys Val Gly│Val Asn Gly Phe Gly Arg Ile Gly│Arg Ile Gly Arg Leu Val Ile
(SEQ ID NO:36)

Human Adult
Brain      -             Val Thr Phe Tyr Thr Asp Ala│Val Ser
(SEQ ID NO:29)

Human IgM Heavy
Chain      -     Glu Val Gln Leu Val Glu Ser│Gly Gly Gly Leu Val Gln Pro Gly│Arg Ser Leu Arg Leu
(SEQ ID NO:37)
```

* Biologically-active fragment (amino acid residue 288-399) produced by *V. cholerae* after processing. The first Gly corresponds to residue 291 of the entire ZOT molecule (Fasano et al, Proc. Natl. Acad. Sci. U.S.A., 88:5242 (1991); and Baudry et al, Infect. Immun., 60(2), 428 (1992)).

PHARMACEUTICAL COMPOSITION AND METHOD FOR INHIBITING GASTROINTESTINAL INFLAMMATION

This application is a divisional application of U.S. patent application Ser. No. 11/074,727, filed Mar. 9, 2005, now U.S. Pat. No. 7,189,696, which is a divisional application of U.S. patent application Ser. No. 10/648,642, filed Aug. 27, 2003, now U.S. Pat. No. 6,936,689, which is a continuation application of U.S. patent application Ser. No. 10/095,450, filed Mar. 13, 2002, now U.S. Pat. No. 6,670,448, which is a divisional application of U.S. patent application Ser. No. 09/127,815, filed Aug. 3, 1998, now U.S. Pat. No. 6,458,925, the disclosures of which are specifically incorporated herein by reference.

The development of the present invention was supported by the University of Maryland, Baltimore, Md. The invention described herein was supported by funding from the National Institutes of Health (NIH DK-48373). The Government has certain rights.

FIELD OF THE INVENTION

The present invention relates to peptide antagonists of zonulin, as well as methods for the use of the same. Said peptide antagonists bind to the zonula occludens receptor, yet do not physiologically modulate the opening of mammalian tight junctions.

BACKGROUND OF THE INVENTION

I. Function and Regulation of Intestinal Tight Junctions

The tight junctions ("tj") or zonula occludens (hereinafter "ZO") are one of the. hallmarks of absorptive and secretory epithelia (Madara, *J. Clin. Invest.*, 83:1089-1094 (1989); and Madara, *Textbook of Secretory Diarrhea* Eds. Lebenthal et al, Chapter 11, pages 125-138 (1990). As a barrier between apical and basolateral compartments, they selectively regulate the passive diffusion of ions and water-soluble, solutes through the paracellular pathway (Gumbiner, *Am. J. Physiol.*, 253 (*Cell Physiol.* 22):C749-C758 (1987)). This barrier maintains any gradient generated by the activity of pathways associated with the transcellular route (Diamond, *Physiologist*, 20:10-18 (1977)).

Variations in transepithelial conductance can usually be attributed to changes in the permeability of the paracellular pathway, since the resistances of enterocyte plasma membranes are relatively high (Madara, supra). The ZO represents the major barrier in this paracellular pathway, and the electrical resistance of epithelial tissues seems to depend on the number of transmembrane protein strands, and their complexity in the ZO, as observed by freeze-fracture electron microscopy (Madara et al, *J. Cell Biol.*, 101:2124-2133 (1985)).

There is abundant evidence that ZO, once regarded as static structures, are in fact dynamic and readily adapt to a variety of developmental (Magnuson et al, *Dev. Biol.*, 67:214-224 (1978); Revel et al, *Cold Spring Harbor Symp. Quant. Biol.* 40:443-455 (1976); and Schneeberger et al, *J. Cell Sci.*, 32:307-324 (1978)), physiological (Gilula et al, *Dev. Biol.*, 50:142-168 (1976); Madara et al, *J. Membr. Biol.*, 100:149-164 (1987); Mazariegos et al, *J. Cell Biol.*, 98:1865-1877 (1984); and Sardet et al, *J. Cell Biol.*, 80:96-117 (1979)), and pathological (Milks et al, *J. Cell Biol.*, 103:2729-2738 (1986); Nash et al, *Lab. Invest.*, 59:531-537 (1988); and Shasby et al, *Am. J. Physiol.*, 255 (*Cell Physiol.*, 24) :C781-C788 (1988)) circumstances. The regulatory mechanisms that underlie this adaptation are still not completely understood. However, it is clear that, in the presence of $Ca^{2+}$, assembly of the ZO is the result of cellular interactions that trigger a complex cascade of biochemical events that ultimately lead to the formation and modulation of an organized network of ZO elements, the composition of which has been only partially characterized (Diamond, *Physiologist*, 20:10-18 (1977)). A candidate for the transmembrane protein strands, occludin, has recently been identified (Furuse et al, *J. Membr. Biol.*, 87:141-150 (1985)).

Six proteins have been identified in a cytoplasmic submembranous plaque underlying membrane contacts, but their function remains to be established (Diamond, supra). ZO-1 and ZO-2 exist as a heterodimer (Gumbiner et al, *Proc. Natl. Acad. Sci., USA*, 88:3460-3464 (1991)) in a detergent-stable complex with an uncharacterized 130 kD protein (ZO-3). Most immunoelectron microscopic studies have localized ZO-1 to precisely beneath membrane contacts (Stevenson et al, *Molec. Cell Biochem.*, 83:129-145 (1988)). Two other proteins, cingulin (Citi et al, *Nature* (London), 333:272-275 (1988)) and the 7H6 antigen (Zhong et al, *J. Cell Biol.*, 120: 477-483 (1993)) are localized further from the membrane and have not yet been cloned. Rab 13, a small GTP binding protein has also recently been localized to the junction region (Zahraoui et al, *J. Cell Biol.*, 124:101-115 (1994)). Other small GTP-binding proteins are known to regulate the cortical cytoskeleton, i.e., rho regulates actin-membrane attachment in focal contacts (Ridley et al, *Cell*, 70:389-399 (1992)), and rac regulates growth factor-induced membrane ruffling (Ridley et al, *Cell*, 70:401-410 (1992)). Based on the analogy with the known functions of plaque proteins in the better characterized cell junctions, focal contacts (Guan et al, *Nature*, 358:690-692 (1992)), and. adherens junctions (Tsukita et al, *J. Cell Biol.*, 123:1049-1053 (1993)), it has been hypothesize that tj-associated plaque proteins are involved in transducing signals in both directions across the cell membrane, and in regulating links to the cortical actin cytoskeleton.

To meet the many diverse physiological and pathological challenges to which epithelia are subjected, the ZO must be capable of rapid and coordinated responses that require the presence of a complex regulatory system. The precise characterization of the mechanisms involved in the assembly and regulation of the ZO is an area of current active investigation.

There is now a body of evidence that tj structural and functional linkages exist between the actin cytoskeleton and the tj complex of absorptive cells (Gumbiner et al, supra; Madara et al, supra; and Drenchahn et al, *J. Cell Biol.*, 107: 1037-1048 (1988)). The actin cytoskeleton is composed of a complicated meshwork of microfilaments whose precise geometry is regulated by a large cadre of actin-binding proteins. An example of how the state of phosphorylation of an actin-binding protein might regulate cytoskeletal linking to the cell plasma membrane is the myristoylated alanine-rich C kinase substrate (hereinafter "MARCKS"). MARCKS is a specific protein kinase C (hereinafter "PKC") substrate that is associated with the cytoplasmic face of the plasma membrane (Aderem, *Elsevier Sci. Pub.* (*UK*), pages 438-443 (1992)). In its non-phosphorylated form, MARCKS crosslinks to the membrane actin. Thus, it is likely that the actin meshwork associated with the membrane via MARCKS is relatively rigid (Hartwig et al, *Nature*, 356:618-622 (1992)). Activated PKC phosphorylates MARCKS, which is released from the membrane (Rosen et al, *J. Exp. Med.*, 172:1211-1215 (1990); and Thelen et al, *Nature*, 351:320-322 (1991)). The actin linked to MARCKS is likely to be spatially separated from the membrane and be more plastic. When MARCKS is dephosphorylated, it returns to the membrane where it once again crosslinks actin (Hartwig et al, supra; and Thelen et al, supra). These data suggest that the F-actin network may be rearranged by a PKC-dependent phosphorylation process that involves actin-binding proteins (MARCKS being one of them).

A variety of intracellular mediators have been shown to alter tj function and/or structure. Tight junctions of amphibian gallbladder (Duffey et al, *Nature*, 204:451-452 (1981)), and both goldfish (Bakker et al, *Am. J. Physiol.*, 246:G213-G217 (1984)) and flounder (Krasney et al, *Fed. Proc.*, 42:1100 (1983)) intestine, display enhanced resistance to passive ion flow as intracellular cAMP is elevated. Also, exposure of amphibian gallbladder to $Ca^{2+}$ ionophore appears to enhance tj resistance, and induce alterations in tj structure (Palant et al, *Am. J. Physiol.*, 245:C203-C212 (1983)). Further, activation of PKC by phorbol esters increases paracellular permeability both in kidney (Ellis et al, *C. Am. J. Physiol.*, 263 (*Renal Fluid Electrolyte Physiol.* 32):F293-F300 (1992)), and intestinal (Stenson et al, *C. Am. J. Physiol.*, 265(*Gastrointest. Liver Physiol.*, 28):G955-G962 (1993)) epithelial cell lines.

II. The Blood-Brain Barrier

The blood-brain barrier (BBB) is an extremely thin membranous barrier that is highly resistant to solute free diffusion, and separates blood and the brain. In molecular dimensions, the movement of drugs or solute through this membrane is essentially nil, unless the compound has access to one of several specialized enzyme-like transport mechanisms that are embebbed within the BBB membranes The BBB is composed of multiple cells rather than a single layer of epithelial cells. Of the four different types of cells that compose the BBB (endothelial cells, perycites, astrocytes, and neurons) the endothelial cell component of the capillaries represents the limiting factor for the permeability of the BBB. The capillary endothetium in vertebrate brain and spinal cord is endowed with tj which closes the interendothelial pores that normally exist in microvascular endothelial barriers in peripheral tissues. Ultimately, endothelial tj are responsible for the limited permeability of the BBB.

III. Zonula Occludens Toxin

Most *Vibrio cholerae* vaccine candidates constructed by deleting the ctxA gene encoding cholera toxin (CT) are able to elicit high antibody responses, but more than one-half of the vaccinees still develop mild diarrhea (Levine et al, *Infect. Immun.*, 56(1):161-167 (1988)). Given the magnitude of the diarrhea induced in the absence of CT, it was hypothesized that *V. cholerae* produce other enterotoxigenic factors, which are still present in strains deleted of the ctxA sequence (Levine et al, supra). As a result, a second toxin, zonula occludens toxin (hereinafter "ZOT") elaborated by *V. cholerae* and which contribute to the residual diarrhea, was discovered (Fasano et al, *Proc. Natl. Acad. Sci., USA*, 8:5242-5246 (1991)). The zot gene is located immediately adjacent to the ctx genes. The high percent concurrence of the zot gene with the ctx genes among *V. cholerae* strains (Johnson et al, *J. Clin. Microb.*, 31/3:732-733 (1993); and Karasawa et al, *FEBS Microbiology Letters*, 106:143-146 (1993)) suggests a possible synergistic role of ZOT in the causation of acute dehydrating diarrhea typical of cholera. Recently, the zot gene has also been identified in other enteric pathogens (Tschape, *2nd Asian-Pacific Symposium on Typhoid fever and other Salomellosis*, 47 (Abstr.) (1994)).

It has been previously found that, when tested on rabbit ileal mucosa, ZOT increases the intestinal permeability by modulating the structure of intercellular tj (Fasano. et al, supra). It has been found that as a consequence of modification of the paracellular pathway, the intestinal mucosa becomes more permeable. It also was found that ZOT does not affect $Na^+$-glucose coupled active transport, is not cytotoxic, and fails to completely abolish the transepithelial resistance (Fasano et al, supra).

More recently, it has been found that ZOT is capable of reversibly opening tj in the intestinal mucosa, and thus ZOT, when co-administered with a therapeutic agent, is able to effect intestinal delivery of the therapeutic agent, when employed in an oral dosage composition for intestinal drug delivery (WO 96/37196; U.S. patent application Ser. No. 08/443,864, filed May. 24, 1995; and U.S. Pat. No. 5,665,389; and Fasano et al, *J. Clin. Invest.*, 99:1158-1164 (1997); each of which is incorporated by reference herein in their entirety). It has also been found that ZOT is capable of reversibly opening tj in the nasal mucosa, and thus ZOT, when co-administered with a therapeutic agent, is able to enhance nasal absorption of a therapeutic agent (U.S. patent application Ser. No. 08/781,057, filed Jan. 9, 1997; which is incorporated by reference herein in its entirety).

In U.S. patent application Ser. No. 08/803,364, filed Feb. 20, 1997; which is incorporated by reference herein in its entirety, a ZOT receptor has been identified and purified from an intestinal cell line, i.e., CaCo2 cells. Further, in U.S. patent application Ser. No. 09/024,198, filed Feb. 17, 1998; which is incorporated by reference herein in its entirety, ZOT receptors from human intestinal, heart and brain tissue have been identified and purified. The ZOT receptors represent the first step of the paracellular pathway involved in the regulation of intestinal and nasal permeability.

IV. Zonulin

In pending U.S. patent application Ser. No. 098/859,931, filed May. 21, 1997, which is incorporated by reference herein in its entirety, mammalian proteins that are immunologically and functionally related to ZOT, and that function as the physiological modulator of mammalian tight junctions, have been identified and purified. These mammalian proteins, referred to as "zonulin", are useful for enhancing absorption of therapeutic agents across tj of intestinal and nasal mucosa, as well as across tj of the blood brain barrier.

In the present invention, peptide antagonists of zonulin have been identified for the first time. Said peptide antagonists bind to ZOT receptor, yet do not function to physiologically modulate the opening of mammalian tight junctions. The peptide antagonists competitively inhibit the binding of ZOT and zonulin to the ZOT receptor, thereby inhibiting the ability of ZOT and zonulin to physiologically modulate the opening of mammalian tight junctions.

SUMMARY OF THE INVENTION

An object of the present invention is to identify peptide antagonists of zonulin.

Another object of the present invention is to synthesize and purify said peptide antagonists.

Still another object of the present invention is to use said peptide antagonists as anti-inflammatory agents in the treatment of gastrointestinal inflammation.

Yet another object of the present invention is to use said peptide antagonists to inhibit the breakdown of the blood brain barrier.

These and other objects of the present invention, which will be apparent from the detailed description of the invention provided hereinafter, have been met, in one embodiment, by a peptide antagonist of zonulin comprising an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, and SEQ ID NO:35, wherein said peptide antagonist binds to a ZOT receptor, yet does not physiologically modulate the opening of mammalian tight junctions.

BRIEF DESCRIPTION OF THE DRAWINGS

FIG. 6 shows a comparison of the N-terminal sequence of zonulin purified from rabbit and various human tissues.

FIG. 7 shows a comparison of the N-terminal sequences of zonulin purified from various human tissues and IgM heavy chain with the N-terminal sequence of the biologically active fragment (amino acids 288-399) of ZOT.

DETAILED DESCRIPTION OF THE INVENTION

Figure 1:
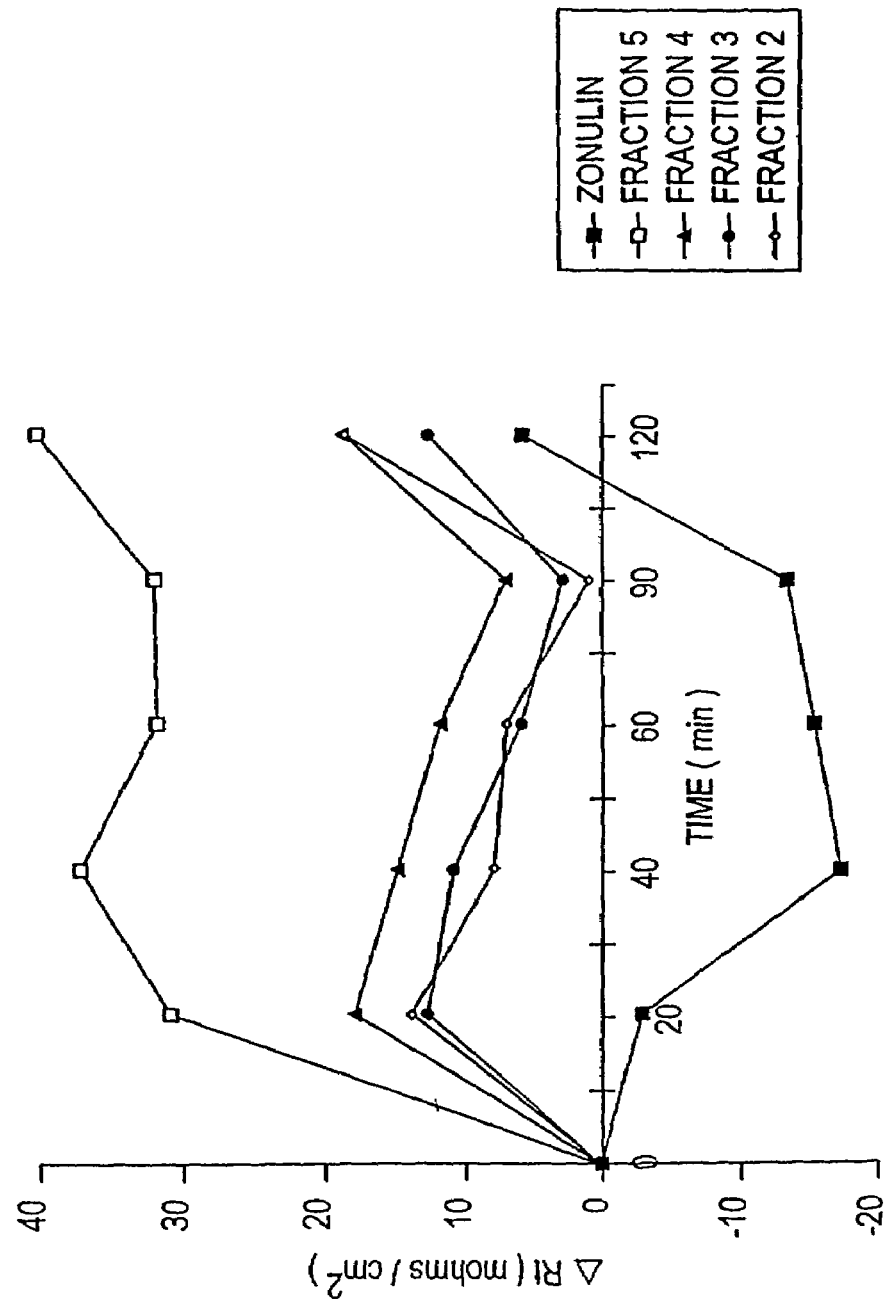
FIG. 1 shows the effect of zonulin purified from rabbit intestine (■), as compared to various negative controls (Fraction 2 (◇); Fraction 3 (●); Fraction 4 (▲); and Fraction 5 (□) from a Q-Sepharose column), on the tissue resistance (Rt) of CaCo2 cell monolayers.

As discussed above, in one embodiment, the above-described object of the present invention have been met by a peptide antagonist of zonulin comprising an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:.8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, and SEQ ID NO:35, wherein said peptide antagonist binds to ZOT receptor, yet does not physiologically modulate the opening of mammalian tight junctions.

The size of the peptide antagonist is not critical to the present invention. Generally, the size of the peptide antagonist will range from 8 to 110, amino acids, preferably from 8 to 40 amino acids, more preferably will be 8 amino acids.

The peptide antagonists can be chemically synthesized and purified using well-known techniques, such as described in *High Performance Liquid Chromatography of Peptides and Proteins:Separation Analysis and Conformation*, Eds. Mant et al, C.R.C. Press (1991), and a peptide synthesizer, such as Symphony (Protein Technologies, Inc); or by using recombinant DNA techniques, i.e., where the nucleotide sequence encoding the peptide is inserted in an appropriate expression vector, e.g., an *E. coli* or yeast expression vector, expressed in the respective host cell, and purified therefrom using well-known techniques.

The peptide antagonists can be used as anti-inflammatory agents for the treatment of gastrointestinal inflammation that gives rise to increased intestinal permeability. Thus, the peptide antagonists of the present invention are useful, e.g. in the treatment of intestinal conditions that cause protein losing enteropathy. Protein losing enteropathy may arise due to:

Infection, e.g., *C. difficile Infection*, enterocolitis, shigellosis, viral gastroenteritis, parasite infestation, bacterial overgrowth, Whipple's disease;

Diseases with mucosal erosion or ulcerations, e.g., gastritis, gastric cancer, collagenous colitis, inflammatory bowel disease;

Diseases marked by lymphatic obstruction, e.g., congenital intestinal lymphangiectasia, sarcoidosis lymphoma, mesenteric tuberculosis, and after surgical correction of congenital heart disease with Fontan's operation;

Mucosal diseases without ulceration, e.g., Ménétrier's disease, celiac disease, eosinophilic gastroenteritis; and Immune diseases, e.g., systemic *lupus erythematosus* or food allergies, primarily to milk (see also Table 40-2 of *Pediatric Gastrointestinal Disease Pathophysiology Diagnosis Management*, Eds. Wyllie et al, Saunders Co. (1993), pages 536-543; which is incorporated by reference herein in its entirety).

Hence, in another embodiment, the present invention relates to a method for treatment of gastrointestinal inflammation comprising administering to a subject in need of such treatment, a pharmaceutically effective amount of a peptide antagonist of zonulin, wherein said peptide antagonist comprises an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, and SEQ ID NO:24, wherein said peptide antagonist binds to the ZOT receptor in the intestine of said subject, yet does not physiologically modulate the opening of tight junctions in said intestine.

To this end, the peptide antagonists can be administered as oral dosage compositions for small intestinal delivery. Such oral dosage compositions for small intestinal delivery are well-known in the art, and generally comprise gastroresistent tablets or capsules (*Remington's Pharmaceutical Sciences*, 16th Ed., Eds. Osol, Mack Publishing Co., Chapter 89 (1980); Digenis et al, *J. Pharm. Sci.*, 83:915-921 (1994); Vantini et al, *Clinica Terapeutica*, 145:445-451 (1993); Yoshitomi et al, *Chem. Pharm. Bull.*, 40:1902-1905 (1992); Thoma et al, *Pharmazie*, 46:331-336 (1991); Morishita et al, *Drug Design and Delivery*, 7:309-319 (1991); and Lin et al, *Pharmaceutical Res.*, 8:919-924 (1991)); each of which is incorporated by reference herein in its entirety).

Tablets are made gastroresistent by the addition of, e.g., either cellulose acetate phthalate or cellulose acetate terephthalate.

Capsules are solid dosage forms in which the peptide antagonist(s) is enclosed in either a hard or soft, soluble container or shell of gelatin. The gelatin used in the manufacture of capsules is obtained from collagenous material by hydrolysis. There are two types of gelatin. Type A, derived from pork skins by acid processing, and Type B, obtained from bones and animal skins by alkaline processing. The use of hard gelatin capsules permit a choice in prescribing a single peptide antagonist or a combination thereof at the exact dosage level considered best for the individual subject. The hard gelatin capsule consists of two sections, one slipping over the other, thus completely surrounding the peptide antagonist. These capsules are filled by introducing the peptide antagonist, or gastroresistent beads containing the peptide antagonist, into the longer end of the capsule, and then slipping on the cap. Hard gelatin capsules are made largely from gelatin, FD&C colorants, and sometimes an opacifying agent, such as titanium dioxide. The USP permits the gelatin for this purpose to contain 0.15% (w/v) sulfur dioxide to prevent decomposition during manufacture.

In the context of the present invention, oral dosage compositions for small intestinal delivery also include liquid compositions which contain aqueous buffering agents that prevent the peptide antagonist from being significantly inactivated by gastric fluids in the stomach, thereby allowing the peptide antagonist to reach the small intestines in an active form. Examples of such aqueous buffering agents which can be employed in the present invention include bicarbonate buffer (pH 5.5 to 8.7, preferably about pH 7.4).

When the oral dosage composition is a liquid composition, it is preferable that the composition be prepared just prior to administration so as to minimize stability problems. In this case, the liquid composition can be prepared by dissolving lyophilized peptide antagonist in the aqueous buffering agent.

The peptide antagonists can be used as to inhibit breakdown of the blood brain barrier. Thus, the peptide antagonists of the present invention are useful, e.g., in the treatment of conditions associated with breakdown of the blood brain barrier. Examples of such conditions include osmotic injuries, e.g., cerebral ischemia, stroke or cerebral edema; hypertension; carbon dioxide; convulsive seizure; chemical toxins; uremia (renal insufficiency); meningitis, encephalitis, encephalomielitis, e.g., infective (viral (SRV, HIV, etc.), or bacterial (TB, *H. influenzae*, meningococcus, etc.) or allergic; tumors; traumatic brain injuries; radiation brain injury; immaturity and kernicterus; demyelinating diseases, e.g., multiple sclerosis or Guillian-Barre syndrome.

Hence, in another embodiment, the present invention relates to a method for treatment of conditions associated with breakdown of the blood brain barrier comprising administering to a subject in need of such treatment, a pharmaceutically effective amount of a peptide antagonist of zonulin, wherein said peptide antagonist comprises amino acid sequence SEQ ID NO:35, wherein said peptide antagonist binds to ZOT receptor in the brain of said subject, yet does not physiologically modulate the opening of tight junctions in said brain.

To this end, the peptide antagonists can be administered as intravenous dosage compositions for delivery to the brain. Such compositions are well-known in the art, and compositions generally comprise a physiological diluent, e.g., distilled water, or 0.9% (w/v) NaCl.

The pharmaceutically effective amount of peptide antagonist employed is not critical to the present invention and will vary depending upon the disease or condition being treated, as well as the age, weight and sex of the subject being treated. Generally, the amount of peptide antagonist employed in the present invention to inhibit gastrointestinal inflammation or inhibit breakdown of the blood brain barrier, e.g., to inhibit zonulin biological activity, is in the range of about $7.5 \times 10^{-6}$ M to $7.5 \times 10^{-3}$ M, preferably about $7.5 \times 10^{-6}$ M to $7.5 \times 10^{-4}$ M. To achieve such a final concentration in, e.g., the intestines or blood, the amount of peptide antagonist in a single oral dosage composition of the present invention will generally be about 1.0 μg to 1000 μg, preferably about 1.0 μg to 100 μg.

The peptide antagonists can be also be used as an immunogen to obtain antibodies, either polyclonal or monoclonal, having binding specificity for zonulin, using techniques well-known in the art (Abrams, *Methods Enzymol.*, 121:107-119 (1986)). These antibodies can in turn can be used to assay for zonulin in body tissue or fluids, or in affinity-purification of zonulin, or alternatively, to bind to zonulin, and thereby inhibit zonulin activity, e.g., to inhibit gastrointestinal inflammation or to inhibit breakdown of the blood brain barrier.

The following examples are provided for illustrative purposes only, and are in no way intended to limit the scope of the present invention.

EXAMPLE 1

Purification of ZOT 5000 ml of the supernatant fraction obtained after culturing *V. cholerae* strain CVD110 (Michalski et al, *Infect. Immun.*, G1:4462-4468 (1993), which had been transformed with plasmid pZ14, was concentrated 1000-fold using a lamina flow filter with a MW cutoff of 10 kDa. The construction of pZ14, which contains the *Vibrio cholera* zot gene, is described in detail in, inter alia, WO 96/37196. The resulting supernatant was then subjected to 8.0% (w/v) SDS-PAGE. Protein bands were detected by Coomassie blue staining of the SDS-PAGE gel. No protein band corresponding to ZOT was detectable when compared to control supernatant from strain CVD110 transformed with plasmid pTTQ181 (Amersham, Arlington Heights, Ill.), and treated in the same manner. Therefore, even though the zot gene was placed behind the highly inducible and strong tac promoter in pZ14, the level of the protein in 1000-fold concentrated pZ14 supernatant was still not detectable by the Coomassie stained SDS-PAGE gel.

A. MBP-ZOT

To increase the amount of ZOT produced, the zot gene was fused in frame with the maltose binding protein (hereinafter "MBP") gene to create a MBP-ZOT fusion protein.

The MBP vector pMAL-c2 (Biolab) was used to express and purify ZOT by fusing the zot gene to the malE gene of *E. coli*. This construct uses the strong, inducible tac promoter, and the malE translation initiation signals to give high level expression of the cloned zot gene. The vector pMAL-c2 has an exact deletion of the malE signal sequence, which leads to cytoplasmic expression of the fusion protein. Affinity chromatography purification for MBP was used to facilitate isolation of the fusion protein (Biolab).

More specifically, vector pMAL-c2 was linearized with EcoRI (that cuts at the 3' end of the malE gene), filled in with Klenow fragment, and digested with XbaI (that has a single site in pMAL-c2 polylinker). The orf encoding ZOT was subcloned from plasmid pBB241 (Baudry et al, *Infect. Immun.*, 60:428-434 (1992)). Plasmid pBB241 was digested with BssHII, filled in with Klenow fragment, and digested with XbaI. Then, the blunt-XbaI fragment was subcloned into pMAL-c2 to give plasmid pLC10-c. Since both the insert, and the vector had blunt and sticky ends, the correct orientation was obtained with the 3' end of malE fused with the 5' terminus of the insert. pLC10-c was then electroporated into *E. coli* strain DH5α. In pBB241, the BssHII restriction site is within the zot orf. Thus, amino acids 1-8 of ZOT are missing in the MBP-ZOT fusion protein.

In order to purify the MBP-ZOT fusion protein, 10 ml of Luria Bertani broth containing 0.2% (w/v) glucose and 100 µg/ml ampicillin were inoculated with a single colony containing pLC10-c, and incubated overnight at 37° C. with shaking. The culture was diluted 1:100 in 1.0 ml of the same fresh medium, and grown at 37° C. while shaking, to about $1.0 \times 10^8$ cells/ml. 0.2 mM IPTG was then added to induce the MBP-ZOT expression, and the culture was incubated at 37° C. for additional 3 hr. The bacteria were then pelleted and resuspended in 20 ml of ice cold "column buffer" comprising 20 mM Tris-HCl, 0.2 M NaCl, 1.0 mM EDTA, 10 mM 2-ME, 1.0 mM $NaN_3$. The bacterial suspension was lysed by french press treatment and spun for 30 min at 13,000×g at 4° C. The supernatant was collected, diluted 1:5 with column buffer and loaded into a 1×10 column of amylose resin (Biolabs, MBP-fusion purification system), pre-equilibrated with column buffer. After washing the column with 5 volumes of column buffer, the MBP-ZOT fusion protein was eluted by loading 10 ml of 10 mM maltose in column buffer. The typical yield from 1.0 ml of culture was 2-3 mg of protein.

The MBP fusion partner of the purified MBP-ZOT fusion protein was then cleaved off using 1.0 µg of Factor Xa protease (Biolabs) per 20 µg of MBP-ZOT. Factor Xa protease cleaves just before the amino terminus of ZOT. The ZOT protein so obtained was run on a 8.0% (w/v) SDS-PAGE gel, and electroeluted from the gel using an electroseparation chamber (Schleicher & Schuell, Keene, N.H.).

When tested in Ussing chambers, the resulting purified ZOT induced a dose-dependent decrease of Rt, with an $ED_{50}$ of $7.5 \times 10^{-8}$ M.

B. 6×His-ZOT

The zot gene was amplified by PCR with Deep Vent polymerase (New England Biolabs), using pBB241 plasmid (Baudry et al, supra) DNA as a template. The forward and reverse primers used were: 5'-CGGGATCCCGTATGAG-TATCTTT-3' (SEQ ID NO:39); and 5'-CCCAAGCT-TGGGTCAAAATATACT-3' (SEQ ID NO:40), respectively. The 5' tails of these oligonucleotides contain a BamHI and a HindIII restriction site, respectively. The resulting amplicon (1.2 kb) was analyzed by 8.0 % (w/v) agarose gel electrophoresis, and purified from salts and free nucleotides using an Xtreme spin column (Pierce). The above-noted two restriction enzymes were then used to digest the purified amplicon, and the resulting digested-amplicon was then inserted in the vector pQE30 (Quiagen), which had been previously digested with BamHI and HindIII, so as to obtain plasmid pSU113. pQE30 is an expression vector that provides high level expression of a recombinant protein with a 6 poly-histidine tag (6×His). The expression product of plasmid pSU113 is therefore a 6×His-ZOT fusion protein. pSU113 was then transformed into *E. coli* DH5α.

In order to purify the 6×His-ZOT fusion protein, the resulting transformed *E. coli* were grown overnight at 37° C. in 150 ml of Luria Bertani broth containing 2.0% (w/v) glucose, 25 µg/ml of kanamycin and 200 µg/ml of ampicillin until the $A_{600}$ was about 1.10. Next, 75 ml of the overnight cultures were added to 1000 ml of Luria Bertani broth containing 2.0% (w/v) glucose, 25 µg/ml of kanamycin and 200 µg/ml of ampicillin, incubated for about 3 hrs at 37° C., with vigorous shaking, until the $A_{600}$ was about 0.7-0.9. Then, IPTG was added to a final concentration of 2.0 mM, and growth was allowed to continue for 5 hrs at 37° C. Next, the cells were harvested by centrifugation at 4000×g for 20 min, the cells resuspend in 5.0 ml/g wet weight of buffer A comprising 6.0 M GuHCl, 0.1 M sodium phosphate, and 0.01 M Tris-HCl (pH. 8.0), and stirred for 1 hr at room temperature. Then, the mixture was centrifuged at 10,000 ×g for .30 min at 4° C., and to the resulting supernatant was added 4.0-5.0 ml/g wet weight of a 50% slurry of SUPERFLOW resin (QIAGEN), and stirring was carried out for 1. hr at room temperature. The resulting resin was loaded into a 1.6×8.0 column, which was then washed sequentially with buffer A, buffer B comprising 8.0 M urea, 0.1 M sodium phosphate, and 0.01 M Tris-HCl (pH 8.0) and buffer C comprising 8.0 M urea, 0.1 M sodium phosphate, and 0.01 M Tris-HCl (pH 6.3). Each wash was carried out until the $A_{600}$ of the flow-through was less than 0.01. The 6×His-ZOT fusion protein was eluted from the column using 20 ml of buffer C containing 250 mM imidazole. Then, the fractions containing with the 6×His-ZOT fusion protein were checked by SDS-PAGE using the procedure described by Davis, *Ann. N.Y. Acad. Sci.*, 121:404 (1964), and the gel stained with Comassie blue. The fractions containing 6×His-ZOT fusion protein were dialyzed against .8.0 M urea, combined, and then diluted 100 times in PBS. Next, 4.0 ml of a 50% slurry of SUPERFLOW resin was added, stirring was carried out for 2 hrs at room temperature, and the resulting resin loaded into a 1.6×8.0 column, which was then washed with 50 ml of PBS. The 6×His-ZOT fusion protein was eluted from the column with 10 ml of PBS containing 250 mM imidazole. The resulting eluant was dialyzed against PBS, and the 6×His-ZOT fusion protein was checked by SDS-PAGE, as described above.

EXAMPLE 2

Production of Affinity-Purified Anti-ZOT Antibodies

To obtain specific antiserum, a chimeric glutathione S-transferase (GST)-ZOT protein was expressed and purified.

More specifically, oligonucleotide primers were used to amplify the zot orf by polymerase chain reaction (PCR) using plasmid pBB241 (Baudry et al, supra) as template DNA. The forward primer (TCATCACGGC GCGCCAGG, SEQ ID NO:25) corresponded to nucleotides 15-32 of zot orf, and the reverse primer (GGAGGTCTAG AATCTGCCCG AT, SEQ ID NO:26) corresponded to the 5' end of ctxA orf. Therefore, amino acids 1-5 of ZOT were missing in the resulting fusion protein. The amplification product was inserted into the polylinker (SmaI site) located at the end of the GST gene in pGEX-2T (Pharmacia, Milwaukee, Wis.). pGEX-2T is a fusion-protein expression vector that expresses a cloned gene as a fusion protein with GST of *Schistosoma japonicum*. The fusion gene is under the control of the tac promoter. Upon induction with IPTG, derepression occurs and GST fusion protein is expressed.

The resulting recombinant plasmid, named pLC11, was electroporated in *E. coli* DH5α. In order to purify GST-ZOT fusion protein, 10 ml of Luria Bertani broth containing 100 µg/ml ampicillin were inoculated with a single colony containing pLC11, and incubated overnight at 37° C. with shaking. The culture was diluted 1:100 in 1.0 ml of the same fresh medium and grown at 37° C. while shaking, to about $1.0 \times 10^8$ cells/ml. 0.2 mM IPTG was then added to induce the GST-ZOT expression, and the culture was incubated at 37° C. for additional 3 hr. The bacteria were then pelleted, resuspended in 20 ml of ice cold PBS (pH 7.4), and lysed by the french press method. The GST-ZOT fusion protein was not soluble under these conditions as it sedimented with the bacterial pellet fraction. Therefore, the pellet was resuspended in Laemli lysis buffer comprising 0.00625 M Tris-HCl (pH 6.8), 0.2 M 2-ME, 2.0% (w/v) SDS, 0.025% (w/v) bromophenol blue and 10% (v/v) glycerol, and subjected to electrophoresis on a 8.0% (w/v) PAGE-SDS gel, and stained with Coomassie brilliant blue. A band of about 70 kDa (26 kDa of GST+44 kDA of ZOT), corresponding to the fusion protein, was electroeluted from the gel using an electroseparation chamber (Schleicher & Schuell, Keene, N.H.).

10 μg of the resulting eluted protein (10-20 μg) was injected into a rabbit mixed with an equal volume of Freund's complete adjuvant. Two booster doses were administered with Freund's incomplete adjuvant four and eight weeks later. One month later the rabbit was bled.

To determine the production of specific antibodies, $10^{-10}$ M of ZOT, along with the two fusion proteins MBP-ZOT and GST-ZOT, was transferred onto a nylon membrane and incubated with a 1:5000 dilution of the rabbit antiserum overnight at 4° C. with moderate shaking. The filter was then washed 15 min 4 times with PBS containing 0.05% (v/v) Tween 20 (hereinafter "PBS-T"), and incubated with a 1:30,000 dilution of goat anti-rabbit IgG conjugated to horseradish peroxidase for 2 hr at room temperature. The filter was washed again for 15 min 4. times with PBS containing 0.1% (v/v) Tween, and immunoreactive bands were detected using enhanced chemiluminescence (Amersham).

On immunoblot, the rabbit antiserum was found to recognize ZOT, as well as MBP-ZOT and GST-ZOT fusion proteins, but not the MBP negative control.

Moreover, to confirm the production of appropriate anti-ZOT antibodies, neutralization experiments were conducted in Ussing chambers. When pre-incubated with pZ14 supernatant at 37° C. for 60 min, the ZOT-specific antiserum (1:100 dilution), was able to completely neutralize the decrease in Rt induced by ZOT on rabbit ileum mounted in Ussing chambers.

Next, the anti-ZOT antibodies were affinity-purified using an MBP-ZOT affinity column. More specifically, a MBP-ZOT affinity column was prepared by immobilizing, overnight at room temperature, 1.0 mg of purified MBP-ZOT, obtained as described in Example 1 above, to a pre-activated gel (Aminolink, Pierce). The column was washed with PBS, and then loaded with 2.0 ml of anti-ZOT rabbit antiserum. After a 90 min incubation at room temperature, the column was washed with 14 ml of PBS, and the specific anti-ZOT antibodies were eluted from the column with 4.0 ml of a solution comprising 50 mM glycine (pH 2.5)., 150 mM NaCl, and 0.1% (v/v) Triton X-100. The pH of the 1.0 ml eluted fractions was immediately neutralized with 1.0 N NaOH.

EXAMPLE 3

Purification of Zonulin

Based upon the observation in U.S. patent application Ser. No. 08/803,364, filed Feb. 20, 1997, that ZOT interacts with a specific epithelial surface receptor, with subsequent activation of a complex intracellular cascade of events that regulate tj permeability, it was postulated in the present invention that ZOT may mimic the effect of a physiological modulator of mammalian tj. It was postulated in U.S. patent application Ser. No. 08/859,931, filed May. 21, 1997, that ZOT, and its physiological analog (zonulin), would be functionally and immunologically related. Therefore, as described therein, affinity-purified anti-ZOT antibodies and the Ussing chamber assay were used in combination to search for zonulin in various rabbit and human tissues.

A. Rabbit Tissues

Initially, zonulin was purified from rabbit intestine. The tissue was disrupted by homogenization in PBS. The resulting cell preparations were than centrifuged at 40,000 rpm for 30 min, the supernatant collected and lyophilized. The resulting lyophilized product was subsequently reconstituted in PBS (10:1 (v/v)), filtered through a 0.45 mm membrane filter, loaded onto a Sephadex G-50 chromatographic column, and eluted with PBS. Then, 2.0 ml fractions obtained from the column were subjected to standard Western immunoblotting using the affinity-purified anti-ZOT antibodies obtained as described in Example 2 above.

Positive fractions, i.e., those to which the anti-ZOT antibodies bound, were combined, lyophilized, reconstituted in PBS (1:1 (v/v)), and subjected to salt gradient chromatography through a Q-Sepharose column. The salt gradient was 0-100% (w/v) NaCl in. 50 mM Tris buffer (pH 8.0). Five 20 ml fractions were collected, and subjected to standard Western immunoblotting using the affinity-purified anti-ZOT antibodies obtained as described in Example 2 above. Fraction 1 (20% (w/v) NaCl) was the only fraction that was found to be positive in the Western immunoblot assay.

The fractions obtained from the Q-Sepharose column were then tested for their tissue resistance effects on both CaCo2 monolayers, and rabbit small intestine in Ussing chambers.

More specifically, CaCo2 cells were grown in cell-culture flasks (Falcon) under humidified atmosphere of 95% $O_2$/5% $CO_2$ at 37° C. in Dulbecco's modified Eagle's medium containing 10% (v/v) fetal-calf serum, 40 μg/l penicillin and 90 μg/l streptomycin. The cells were subcultured at a surface ratio of 1:5 after trypsin treatment every 5 days, when they had reached 70-80% confluence. The passage number of the cells used in the this study varied between 15 and 30.

The CaCo2 monolayers were grown to confluence (12-14 days after plating at a 1:2.5 surface ratio) on tissue-culture-treated polycarbonate filters firmly attached to a polystyrene ring (6.4 mm diameter, Transwell Costar). The filters were placed in a tightly fitting insert separating the serosal and mucosal compartment of a modified Ussing chamber, and the experiments were carried out as described by Fasano et al, *Proc. Natl. Acad. Sci., USA*, 8:5242-5246 (1991), for rabbit intestines in Ussing chambers. The results are shown in FIG. 1.

As shown in FIG. 1, the zonulin-containing fraction induced a significant reduction of CaCo2 monolayers' resistance, as compared to zonulin-negative fractions.

Next, Ussing chamber assays were carried out using ileum from 2-3 kg adult male New Zealand white rabbits, which were sacrificed by cervical dislocation. A 20 cm segment of ileum was removed, rinsed free of the intestinal content, opened along the mesenteric border, and stripped of muscular and serosal layers. Eight sheets of mucosa so prepared were then mounted in lucite Ussing chambers (1.12 $cm^2$ opening), connected to a voltage clamp apparatus (EVC 4000 WPI, Saratosa, Fla.), and bathed with freshly prepared Ringer's solution comprising 53 mM NaCl, 5.0 mM KCl, 30.5 mM mannitol, 1.69 mM $Na_2HPO_4$, 0.3 mM $NaH_2PO_4$, 1.25 mM $CaCl_2$, 1.1 mM $MgCl_2$, and 25 mM $NaHCO_3$. The bathing solution was maintained at 37° C. with water-jacketed reservoirs connected to a constant-temperature circulating pump and gassed with 95% $O_2$/5% $CO_2$.

100 μl of zonulin purified from rabbit intestine was added to the mucosal side. The potential difference (PD) was measured every 10 min, and the short-circuit current (Isc) and tissue resistance (Rt) were calculated as described by Fasano et al, supra. Because of tissue variability, data were calculated as ΔRt (Rt at time x)−(Rt at time 0). The results are shown in FIG. 2.

Figure 2:
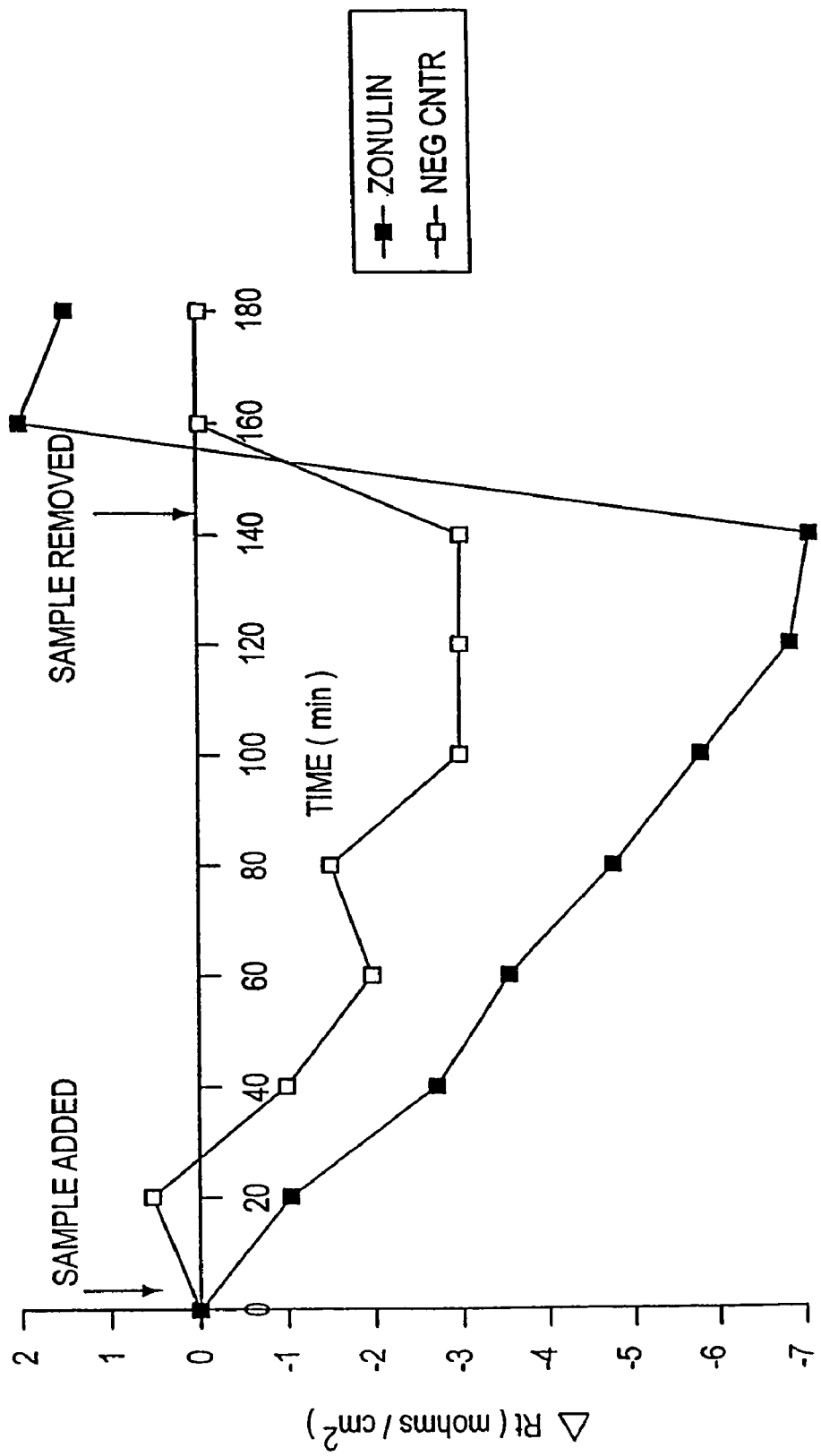
FIG. 2 shows the effect of zonulin purified from rabbit intestine (■), as compared to the negative control (□), on the tissue resistance (Rt) of rabbit ileum mounted in Ussing chambers.

As shown in FIG. 2, the zonulin-containing fraction induced a significant reduction in rabbit small intestinal resistance, as compared to a zonulin-negative fraction. This effect was completely reversible once zonulin was withdrawn from the reservoir.

The zonulin-positive fraction was also subjected to 8.0% (w/v) SDS-PAGE, followed by Western immunoblotting using the anti-ZOT antibodies. The protein bands separated by SDS-PAGE were then transferred onto PVDF filter (Millipore) using CAPS buffer comprising 100 ml of (3-[cyclohexylamino]-1 propanesulfonic acid) 10×, 100 ml of methanol, 800 ml of distilled water. The protein that aligned to a single band that was detected by Western immunoblotting had an apparent molecular weight of about 47 kDa. This band was cut out from the PVDF filter, and subjected to N-terminal sequencing as described by Hunkapiller, In: *Methods of Protein Microcharacterization*, Ed. Shibley, Chapters 11-12, Humana Press, pages 315-334 (1985), using a Perkin-Elmer Applied Biosystems Apparatus Model 494. The N-terminal sequence of zonulin purified from rabbit intestine is shown in SEQ ID NO:27.

The rabbit zonulin N-terminal sequence was compared to other protein sequences by BLAST search analysis. The result of this analysis revealed that the N-terminal sequence of rabbit zonulin is 85% identical, and 100% similar, to the N-terminal sequence of tau protein from *Homo sapiens*.

As a result, to determine whether rabbit zonulin and tau are the same moiety, cross-neutralization experiments were conducted in Ussing chambers. More specifically, 10 μl/ml of rabbit zonulin was added to the mucosal side of rabbit ileum either untreated or pre-incubated for 60 min at 37° C. with anti-tau antibodies (dilution 1:10) (Sigma). Both 10 μl/ml of rabbit zonulin pre-incubated with anti-ZOT antibodies (dilution 1:10) (Example 2); and 0.4 μg/ml of purified tau (Sigma), were used as controls. The results are shown in FIG. 3.

Figure 3:
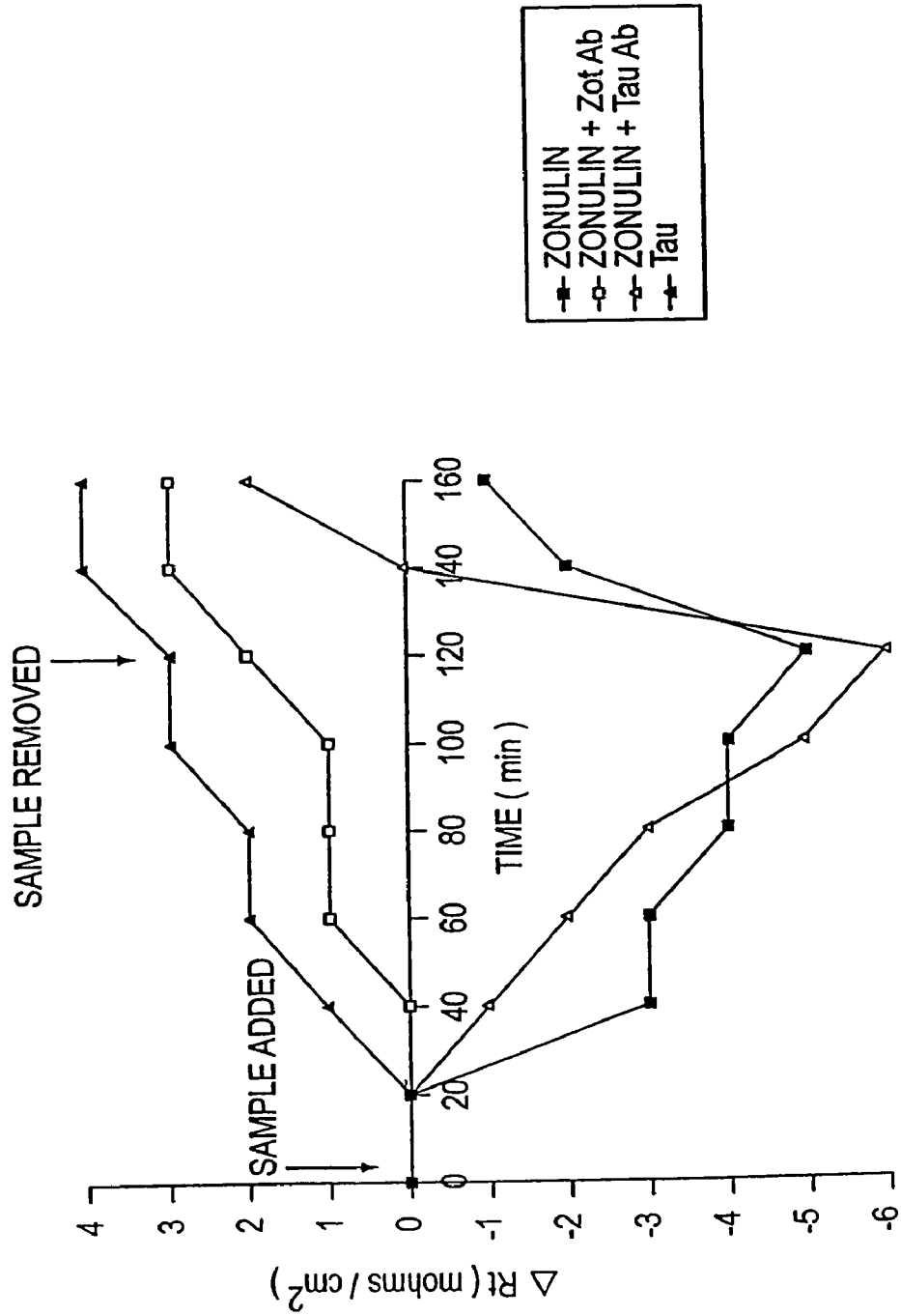
FIG. 3 shows the effect of zonulin purified from rabbit intestine (■), as compared to the negative controls (zonulin+anti-ZOT antibody (□); zonulin+anti-tau antibody (Δ); and tau (▲), on the tissue resistance (Rt) of rabbit ileum mounted in Ussing chambers.

As shown in FIG. 3, rabbit zonulin induced the typical decrease of tissue resistance that was readily reversible once the protein was withdrawn from the Ussing chambers. This activity was completely neutralized by pre-treatment with anti-ZOT antibodies, but not by pre-treatment with anti-tau antibodies. On the other hand, there was no significant effect on tissue resistance in tissues exposed to tau protein.

Rabbit zonulin was also detected in various other rabbit tissues, i.e., rabbit heart, brain, muscle, stomach, spleen, lung, kidney, as well as various portions of rabbits intestines, i.e., distal jejunum, proximal jejunum, ileum, caecum and colon. That is, when these rabbit tissues were processed in the same manner as the rabbit intestine, discussed above, and subjected to 8.0% (w/v) SDS-PAGE, followed by Western immunoblotting using affinity-purified anti-ZOT antibodies obtained as described in Example 2 above, a single band of approximately 47 kDa in size was detected in all of the tissues tested.

B. Human Tissues

Zonulin was also purified from several human tissues, including intestine, heart, and brain. Both fetal and adult tissues were used. The tissues were disrupted by homogenization in PBS. The resulting cell preparations were than centrifuged at 40,000 rpm for 30 min, the supernatant collected and lyophilized. The resulting lyophilized product was subsequently reconstituted in PBS (10:1 (v/v)), filtered through a 0.45 mm membrane filter, loaded onto a Sephadex G-50 chromatographic column, and eluted with PBS. Then, 2.0 ml fractions obtained from the column were subjected to standard Western immunoblotting using the affinity-purified anti-ZOT antibodies obtained as described in Example 2 above.

Positive fractions, i.e., those to which the anti-ZOT antibodies bound, were combined, lyophilized, reconstituted in PBS (1:1 (v/v)), and subjected to salt gradient chromatography through a Q-Sepharose column. The salt gradient was 0-100% (w/v) NaCl in 50 mM Tris buffer. (pH 7.4). Five 20 ml fractions were collected, and subjected to standard Western immunoblotting using the affinity-purified anti-ZOT antibodies obtained as described in Example 2 above. Fraction 1 (20% (w/v) NaCl) showed a single band of 47 kDa in size in the Western immunoblot assay. Fraction 2 (40% (w/v) NaCl) showed two additional bands of 35 kDa and 15 kDa in size in the Western immunoblot assay. Fraction 3 (60% (w/v) NaCl) and Fraction 4 (80% (w/v) showed only the 35 kDa and 15 kDa bands. These results suggest that zonulin may be subjected to degradation by proteases, probably present in the human tissues used, and that the breakdown products elute from the column at higher salt concentrations as compared to the holoprotein.

Fraction 1 (from human heart, intestine and brain tissues) and Fraction 4 (from heart tissue) obtained from the Q-Sepharose column were then tested for their tissue resistance effects on both rabbit intestine and Rhesus monkey intestine in Ussing chambers.

Ussing chamber assays were carried out using different tracts of intestine, including jejunum, ileum, or colon from either 2-3 kg adult male New Zealand white rabbits, or 5-6 kg adult male Rhesus monkeys. After the animals were sacrificed, different segments of intestine, including jejunum, ileum, and colon, were removed, rinsed free of the intestinal content, opened along the mesenteric border, and stripped of muscular and serosal layers. Eight sheets of mucosa so prepared (three jejunum, three ileum, and two colon) were then mounted in lucite Ussing chambers (1.12 cm$^2$ opening), connected to a voltage clamp apparatus (EVC 4000 WPI, Saratosa, FL), and bathed with freshly prepared Ringer's solution comprising 53 mM NaCl, 5.0 mM KCl, 30.5 mM mannitol, 1.69 mM Na$_2$HPO$_4$, 0.3 mM NaH$_2$PO$_4$, 1.25 mM CaCl$_2$, 1.1 mM MgCl$_2$, and 25 mM NaHCO$_3$. The bathing solution was maintained at 37° C. with water-jacketed reservoirs connected to a constant-temperature circulating pump and gassed with 95% O$_2$/5% CO$_2$.

100 μl of Fraction 1 of zonulin purified from human heart or Fraction 1 of zonulin purified from human brain, or Fraction 1 of zonulin purified from human intestine, or Fraction 4 purified from human heart, was added to the mucosal side. The potential difference (PD) was measured every 10 min, and the short-circuit current (Isc) and tissue resistance (Rt) were calculated as described by Fasano et al, supra. Data were calculated as Rt for FIGS. 4A and 4B; but because of tissue variability, data were calculated as ΔRt (Rt at time x)−(Rt at time 0) for FIGS. 5A and 5B. The results are shown in FIGS. 4A and 4B (monkey intestine) and FIGS. 5A and 5B (rabbit intestine).

Figure 4A:
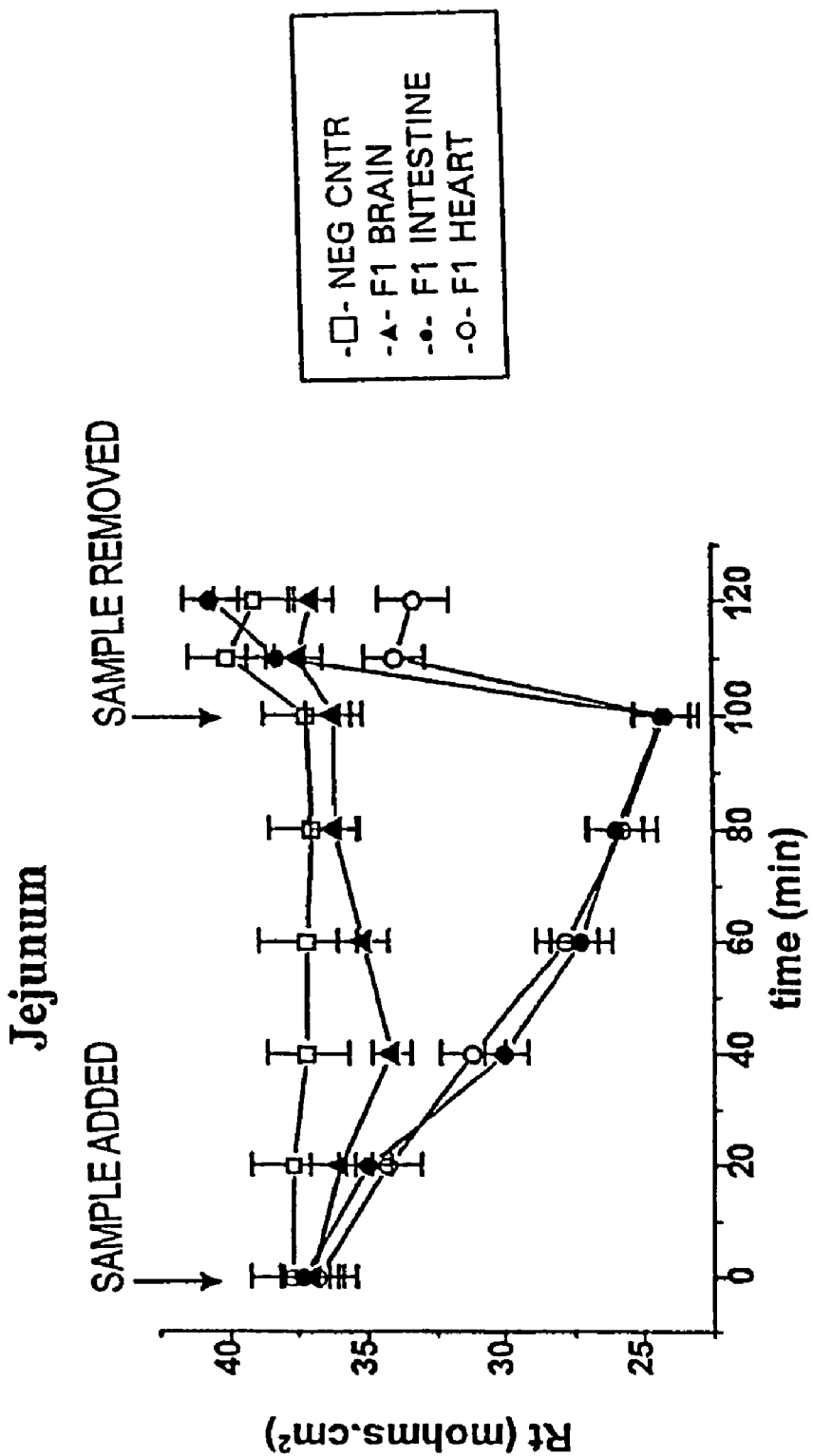
FIGS. 4A and 4B show the effect of zonulin purified from either human brain (▲), human intestine (●), or human heart (○), as compared to the negative control (□), on the tissue resistance (Rt) of Rhesus monkey jejunum (FIG. 4A) and Rhesus monkey ileum (FIG. 4B) mounted in Ussing chambers.
Figure 4B:
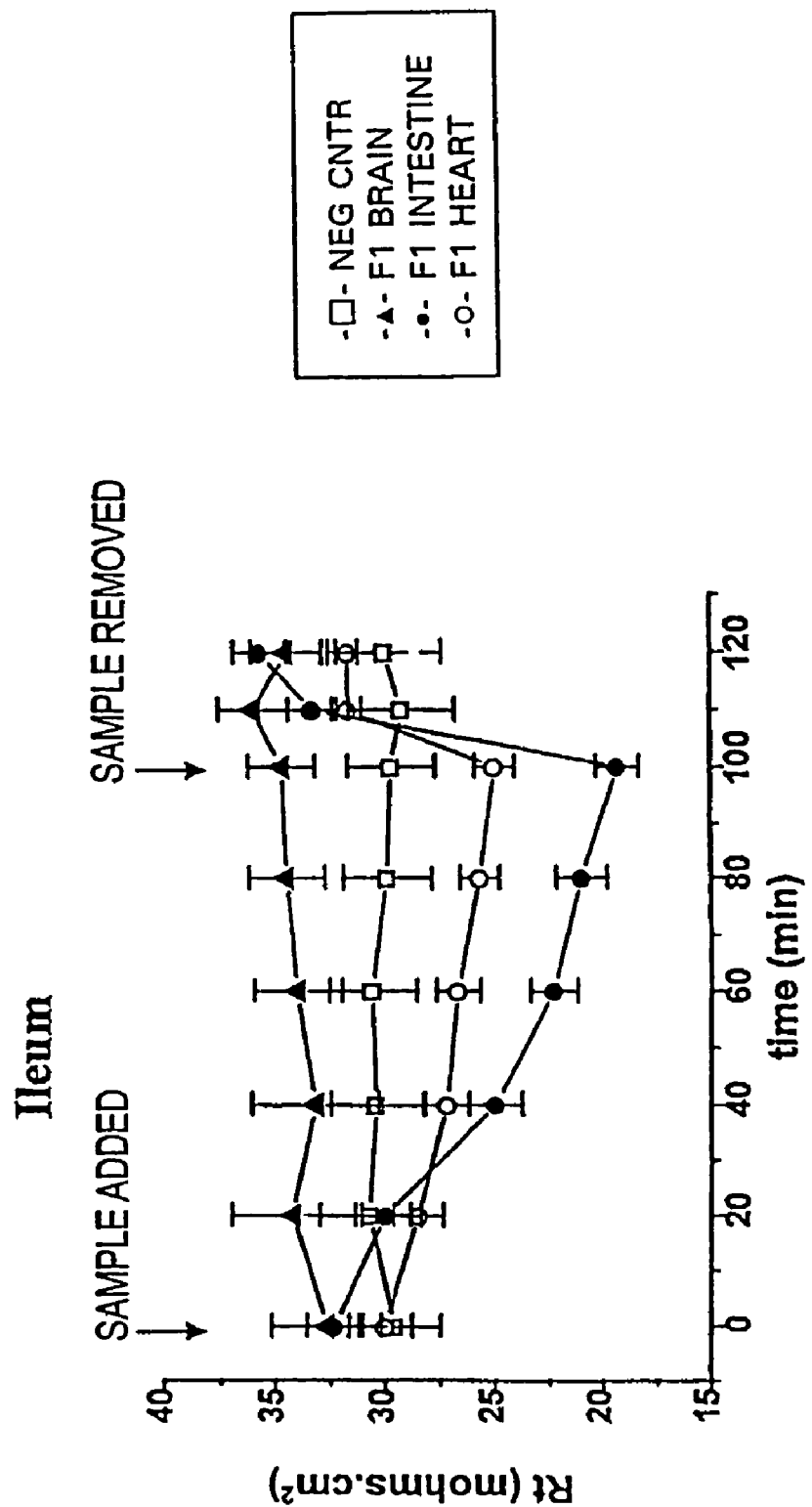

As shown in FIGS. 4A and 4B, zonulin purified from human heart and intestine (Fraction 1) induced a significant reduction in monkey intestinal resistance (both jejunum (FIG. 4A) and ileum (FIG. 4B), as compared to the PBS negative control. No significant changes were observed when zonulin purified from either human heart or human intestine were tested in the colon. FIGS. 4A and 4B also show that no significant effect on both monkey jejunum (FIG. 4A) and monkey ileum (FIG. 4B) was observed when zonulin purified from human brain (Fraction 1) was tested. Fraction 4 of zonulin purified from human heart also induced a significant decrease in monkey small intestinal tissue resistance.

Figure 5A:
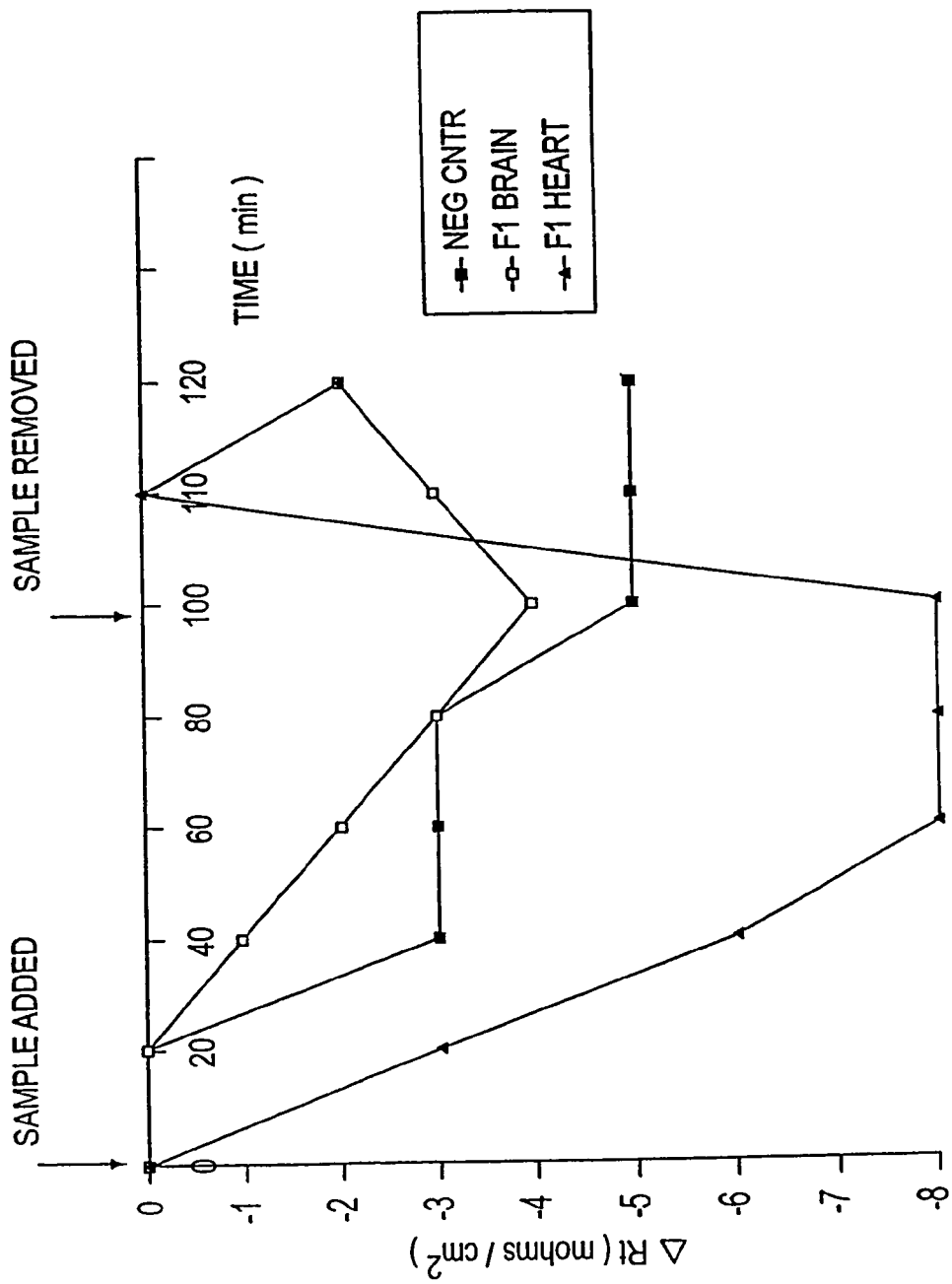
FIGS. 5A and 5B show the effect of zonulin purified from either human heart (▲) or human brain (□), as compared to the negative control (■), on the tissue resistance (Rt) of rabbit jejunum (FIG. 5A) and rabbit ileum (FIG. 5B) mounted in Ussing chambers.
Figure 5B:
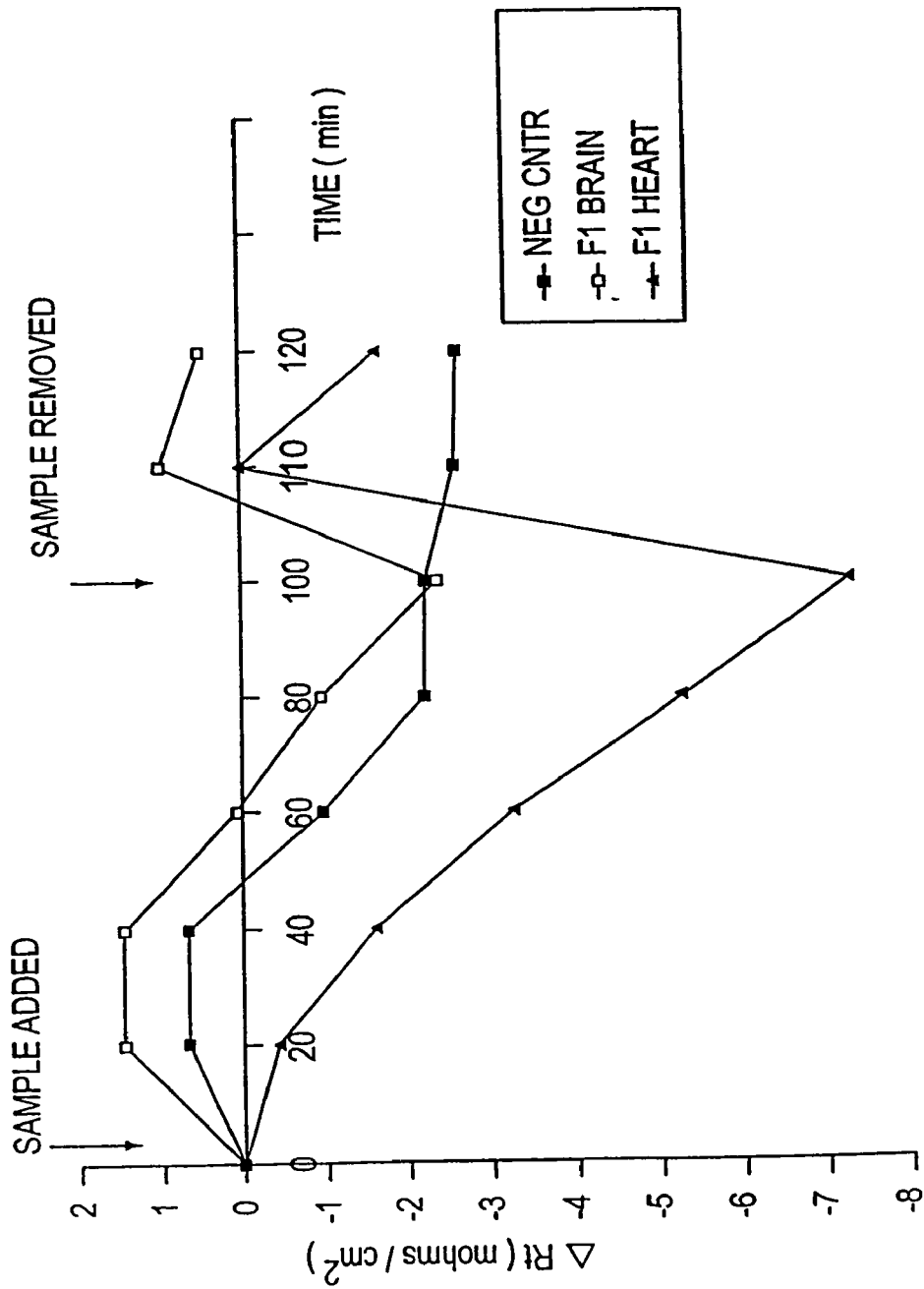

As shown in FIGS. 5A and 5B, similar results were obtained when rabbit intestine was used. That is, zonulin purified from human heart (Fraction 1) showed a significant effect on tissue resistance both in the rabbit jejunum (FIG. 5A) and rabbit ileum (FIG. 5B), but not in the colon. FIGS. 5A and 5B also show that no significant effect on both rabbit jejunum (FIG. 5A) and rabbit ileum (FIG. 5B) was observed when zonulin purified from human brain (Fraction 1) was tested.

To establish whether zonulin increases the oral delivery of insulin, in vitro model experiments using rabbit intestine were performed. Briefly, adult male New Zealand white rabbits (2-3 kg) were sacrificed by cervical dislocation. Segments of rabbit small intestine (either jejunum or ileum) were removed, rinsed free of the intestinal content, opened along the mesenteric border, and stripped of muscular and serosal layers. Eight sheets of mucosa so prepared were then mounted in Lucite Ussing chambers (1.12 cm$^2$ opening), connected to a voltage clamp apparatus (EVC 4000 WPI, Sarasota, Fla.), and bathed with freshly prepared buffer containing 53 mM NaCl, 5.0 mM KCl, 30.5 mM mannitol, 1.69 mM $Na_2HPO_4$, 0.3 mM $NaH_2PO_4$, 1.25 mM $CaCl_2$, 1.1 mM $MgCl_2$, and 25 mM $NaHCO_3$. The bathing solution was maintained at 37° C. with water-jacketed reservoirs connected to a constant-temperature circulating pump and gassed with 95% $O_2$/5% $CO_2$. Potential difference (PD) was measured, and short-circuit current (Isc) and tissue resistance (Rt) were calculated. Once the tissues reached a steady state condition, paired tissues, matched on the basis of their resistance, were exposed luminally to $10^{-11}$ $M^{125}$I-insulin (Amersham, Arlington Heights, Ill.; 2.0 µCi=$10^{-12}$ M), alone or in the presence of 100 µl of heart zonulin from Fraction 1. A 1.0 ml aliquot from the serosal side and a 50 µl aliquot from the mucosal side were immediately obtained to establish baseline values. Samples from the serosal side were then collected at 20 min intervals for the following 100 min.

It was found that heart zonulin increased the intestinal absorption of insulin both in the jejunum (0.058±0.003 fmol/cm$^2$.min vs. 0.12±0.005 fmol/cm$^2$.min, untreated vs. zonulin-treated tissues, respectively, p=0.001), and in the ileum (0.006±0.0002 fmol/cm$^2$.min vs. 0.018±0.005 fmol/cm$^2$.min, untreated vs. zonulin-treated tissues, respectively, p=0.05) in a time-dependent manner.

Fraction 1 of zonulin purified from human heart, Fraction 1 of zonulin purified from human intestine, and Fraction 1 of zonulin purified from human brain were also subjected to 8.0% (w/v) SDS-PAGE, followed by Western immunoblotting using the anti-ZOT antibodies obtained as described in Example 2 above. The protein bands separated by SDS-PAGE were then transferred onto PVDF filter using CAPS buffer comprising 100 ml of (3-[cyclohexylamino]-1 propanesulfonic acid) 10×, 100 ml of methanol, 800 ml of distilled water. The protein that aligned to a single band that was detected by Western immunoblotting had an apparent molecular weight of about 47 kDa. This band was cut out from the PDVF filter, and subjected to N-terminal sequencing as described by Hunkapiller, In: *Methods of Protein Microcharacterization*, Ed. Shibley, Chapters 11-12, Humana Press, pages 315-334 (1985), using a Perkin-Elmer Applied Biosystems Apparatus Model 494. The N-terminal sequence of zonulin purified from adult human heart is shown in SEQ ID NO:28, the N-terminal sequence of zonulin purified from adult human brain is shown in SEQ ID NO:29, and the N-terminal sequence of zonulin purified from adult fetal brain is shown in SEQ ID NO:36.

The first nine amino acids from the N-terminal sequence of zonulin purified from adult human intestine (SEQ ID NO:31) were also sequenced, and found to be identical to the first nine amino acids of zonulin purified from human heart shown in SEQ ID NO:28 (see FIG. 6). The first twenty amino acids from the N-terminal sequence of zonulin purified from human fetal intestine were also sequenced: Met Leu Gln Lys Ala Glu Ser Gly Gly Val Leu Val Gln Pro Gly Xaa Ser Asn Arg Leu (SEQ ID NO:30), and found to be almost identical to the amino acid sequence of zonulin purified from human heart shown in SEQ ID NO:28 (see FIG. 6).

The N-terminal sequence of zonulin purified from adult human brain (SEQ ID NO:29) and fetal human brain (SEQ ID NO:36) was completely different than the N-terminal of zonulin purified from each of heart (SEQ ID NO:28), fetal intestine (SEQ ID NO:30) and adult intestine (SEQ ID NO:31) (see FIGS. 6-7). This difference is believed to explain the tissue-specificity of zonulin in determining the permeability of tissues, such as the intestine, demonstrated above.

The N-terminal sequences of human zonulin purified from heart, intestine, and brain, all differ from the N-terminal sequence of zonulin purified from rabbit intestine (FIG. 6). To establish whether these proteins represent different isoforms of a tau-related family of proteins, tissues from both rabbit and human were subjected to 8.0% (w/v) SDS-PAGE, followed by Western immunoblotting using either anti-ZOT or anti-tau antibodies. The 47 kDa zonulin bands purified from both rabbit and human tissues (including brain, intestine, and heart) which were found to be recognized by the anti-ZOT antibodies, were also found to cross-react with anti-tau antibodies. The different fractions of zonulin purified from human brain obtained by salt chromatography were also subjected to Western immunoblotting using either anti-ZOT antibodies or anti-tau antibodies. While anti-ZOT antibodies recognized the intact 47 kDa protein and both of the 35 kDa and 15 kDa breakdown fragments, the anti-tau antibodies only recognized the intact 47 kDa protein and the 35 kDa fragment, while the anti-tau antibodies did not recognize the 15 kDa fragment. To establish whether the 35 kDa fragment includes the N-terminus or the C-terminus of zonulin, the N-terminal sequence of the 35 kDa band was obtained and found to be: Xaa Xaa Asp Gly Thr Gly Lys Val Gly Asp Leu (SEQ ID NO:32). This sequence is different from the N-terminal sequence of the intact human brain zonulin (SEQ ID NO:29). These results suggest that the 15 kDa fragment represents the N-terminal portion of zonulin, while the 35 kDa fragment represents the C-terminal portion of zonulin.

Combined together, these results suggest that the zonulin domain recognized by the anti-tau antibodies is toward the C-terminus of the protein, is common to the different isoforms of zonulin from either human or rabbit tissues (while the N-terminal portion may vary), and is probably involved in the permeabilizing effect of the protein (based on the observation that tau binds to β-tubulin with subsequent rearrangement of the cell cytoskeleton, and the effect of Fraction 4 on monkey small intestinal tissue resistance).

The N-terminal sequence of human zonulin purified from both the heart and intestine was compared to other protein sequences by BLAST search analysis. The result of this analysis revealed that the N-terminal sequence of human zonulin is 95% identical, to the N-terminal sequence of the heavy variable chain of IgM from *Homo sapiens* (SEQ ID NO:37).

As a result, to determine whether human zonulin purified from heart and human IgM are the same moiety, a partial digestion of the human zonulin was performed to obtain an internal fragment, which was then sequenced.

More specifically, 1.0 mm of the PVDF filter containing zonulin purified from human heart was placed in a plastic tube previously washed with 0.1% (w/v) trifluoracetic acid (TFA), and rinsed with methanol. 75 µl of a buffer solution comprising 100 mM Tris (pH 8.2), 10% (v/v) $CH_3CN$, and 1.0% (v/v) dehydrogenated Triton X-100 was added, and incubated with the membrane at 37° C. for 60 min. 150 ng of trypsin was then added, and an additional 24 hr incubation period at 37° C. was carried out. The resulting solution was sonicated for 10 min, and the supernatant decanted. 75 µl of 0.1% (w/v) TFA was then added, the solution was sonicated for additional 10 min, and the supernatant decanted. Both aliquots were loaded on a 0.5 mm×250 mm $C_{18}$ column, 5.0 µm particle size, 300 Å pore size. A gradient from 0.1% (w/v) TFA to 45% $CH_3CN$ water+0.1% (w/v) TFA was developed for 2 hr and 15 min. The peaks were finally collected and sequenced.

The internal sequence of human zonulin purified from adult human heart was found to be: Leu Ser Glu Val Thr Ala Val Pro Ser Leu Asn Gly Gly (SEQ ID NO:33).

The human zonulin internal sequence was compared to other protein sequences by BLAST search analysis. The result of this analysis revealed that the internal sequence of human zonulin has 0% identity to any internal sequence of the heavy variable chain of IgM from *Homo sapiens*.

The results in Example 3 above demonstrate that (1) zonulin represents the physiological modulator of the paracellular pathway; (2) the N-terminal sequence of rabbit zonulin is highly homologous to the N-terminal sequence of the tau protein; (3) zonulin and tau are two distinct moieties that are immunologically related, yet functionally different; (4) the N-terminal sequence of human zonulin obtained from heart and intestine is highly homologous to the N-terminal sequence of the heavy chain of the variable region of IgM; (5) human zonulin and IgM are two distinct moieties that are structurally related, yet functionally different; and (6) zonulin represents a family of tau-related proteins with common, active C-terminal sequences, and variable N-terminal sequences.

EXAMPLE 4

Peptide Antagonists of Zonulin

Given that ZOT, human intestinal zonulin (zonulin$_i$) and human heart zonulin (zonulin$_h$) all act on intestinal (Fasano et al, *Gastroenterology*, 112:839 (1997); Fasano et al,. *J. Clin. Invest.*, 96:710 (1995); and FIGS. 1-5) and endothelial tj and that all three have a similar regional effect (Fasano et al (1997), supra; and FIGS. 1-5) that coincides with the ZOT receptor distribution within the intestine (Fasano et al (1997), supra; and Fasano et al (1995), supra), it was postulated in the present invention that these three molecules interact with the same receptor binding site. A comparison of the primary amino acid structure of ZOT and the human zonulins was thus carried out to provide insights as to the absolute structural requirements of the receptor-ligand interaction involved in the regulation of intestinal tj. The analysis of the N-termini of these molecules revealed the following common motif (amino acid residues 8-15 boxed in FIG. 7): non-polar (Gly for intestine, Val for brain), variable, non-polar, variable, non-polar, polar, variable, polar (Gly). Gly in position 8, Val in position 12 and Gln in position 13, all are highly conserved in ZOT, zonulin$_i$ and zonulin$_h$ (see FIG. 7), which is believed to be critical for receptor binding function within the intestine. To verify the same, the synthetic octapeptide Gly Gly Val Leu Val Gln Pro Gly (SEQ ID NO:15) (named FZI/0, and corresponding to amino acid residues 8-15 of human fetal zonulin$_i$) was chemically synthesized.

Next, rabbit ileum mounted in Ussing chambers as described above, were exposed to 100 µg of FZI/0 (SEQ ID NO:15), 100 µg of FZI/1 (SEQ ID NO:34), 1.0 µg of 6×His-ZOT (obtained as described in Example 1), 1.0 µg of zonulin$_i$, (obtained as described in Example 3), or 1.0 µg of zonulin$_h$ (obtained as described in Example 3) alone; or pre-exposed for 20 min to 100 µg of FZI/0 or FZI/1, at which time 1.0 µg of 6×His-ZOT, 1.0 µg of Zonulin$_i$, or 1.0 µg of zonulin$_h$, was added. ΔRt was then calculated as described above. The results are shown in FIG. 8.

Figure 8:
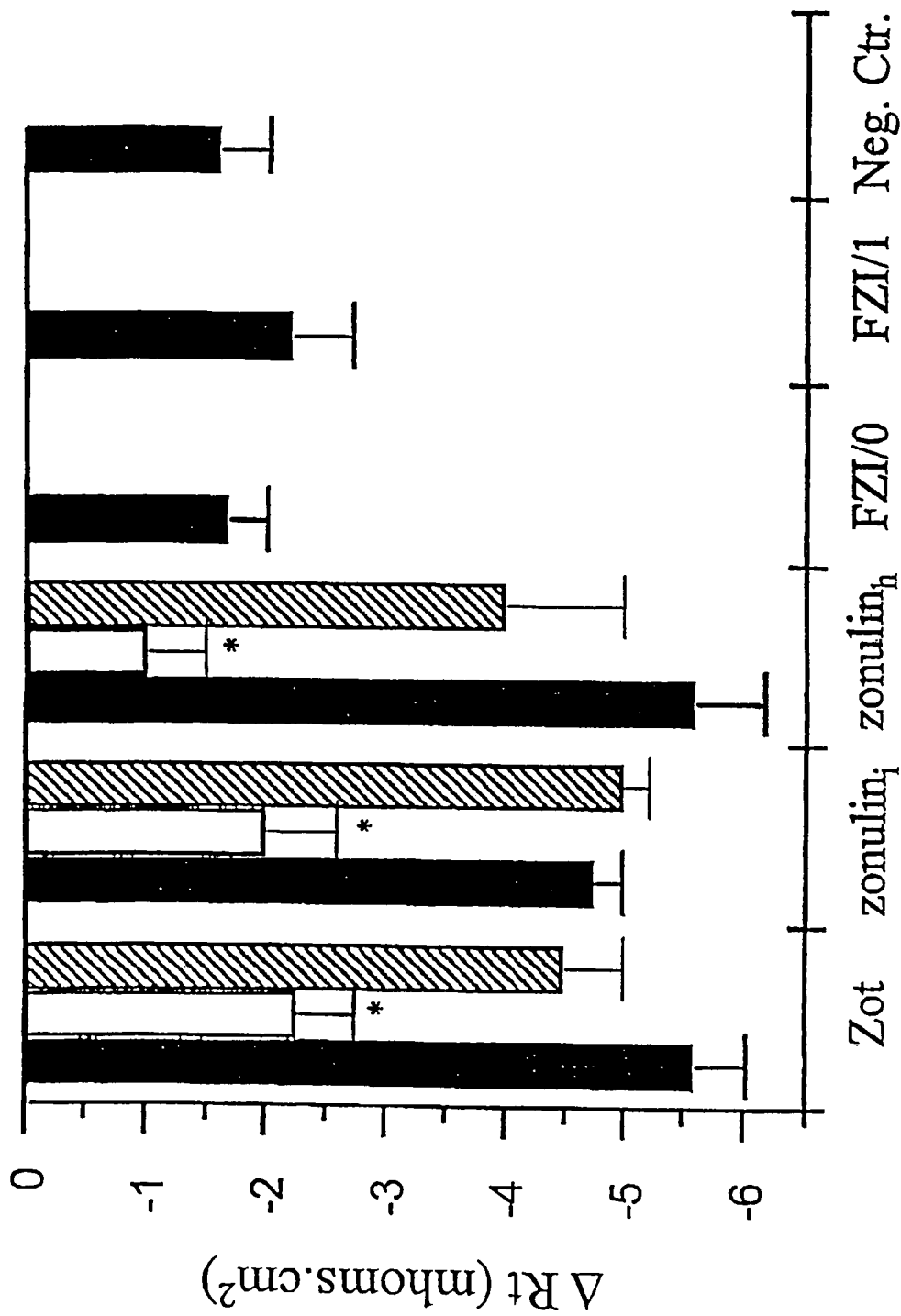
FIG. 8 shows the effect of ZOT, zonulin$_i$, zonulin$_h$, either alone (closed bars), or in combination with the peptide antagonist FZI/0 (open bars) or in combination with FZI/1 (shaded bars), as compared to the negative control, on the tissue resistance (Rt) of rabbit ileum mounted in Ussing chambers. N equals 3-5; and * equals p<0.01.

As shown in FIG. 8, FZI/0 did not induce any significant change in Rt (0.5% as compared to the negative control) (see closed bar). On the contrary, pre-treatment for 20 min with FZI/0 decreased the effect of ZOT, zonulin$_i$, and zonulin$_h$ on Rt by 75%, 97%, and 100%, respectively (see open bar). Also as shown in FIG. 8, this inhibitory effect was completely ablated when a second synthetic peptide (FZI/1) was chemically synthesized by changing the Gly in position 8, the Val in position 12, and the Gln in position 13 (as referred to zonulin$_i$) with the correspondent amino acid residues of zonulin$_h$ (Val, Gly, and Arg, respectively) was used (see shaded bar).

The above results demonstrate that there is a region spanning between residue 8 and 15 of the N-terminal end of ZOT and the zonulin family that is crucial for the binding to the target receptor, and that the amino acid residues in position 8, 12, and 13 determine the tissue specificity of this binding.

While the invention has been described in detail, and with reference to specific embodiments thereof, it will be apparent to one of ordinary skill in the art that various changes and modifications can be made therein without departing from the spirit and scope thereof.

What is claimed is:

1. A pharmaceutical composition for treating intestinal inflammation comprising an effective amount of a peptide, the amino acid sequence of the peptide consisting of SEQ ID NO:15.

2. The pharmaceutical composition of claim 1, wherein the composition is an oral dosage composition.

3. The pharmaceutical composition of claim 2, wherein the oral dosage composition is formulated for delivery to the small intestine.

4. The pharmaceutical composition of claim 3, wherein the pharmaceutical composition is a tablet.

5. The pharmaceutical composition of claim 4, wherein the tablet is gastroresistant.

6. The pharmaceutical composition of claim 3, wherein the composition is a capsule.

7. The pharmaceutical composition of claim 6, wherein the capsule is gastroresistant.

8. The pharmaceutical composition of claim 6, wherein the capsule comprises at least one bead.

9. The pharmaceutical composition of claim 8, wherein the bead is gastroresistant.

10. A purified peptide consisting of SEQ ID NO: 15.

* * * * *

SEQUENCE LISTING

<160> NUMBER OF SEQ ID NOS: 40

<210> SEQ ID NO 1
<211> LENGTH: 8
<212> TYPE: PRT
<213> ORGANISM: Artificial Sequence
<220> FEATURE:
<223> OTHER INFORMATION: Zonulin Peptide Antagonist

<400> SEQUENCE: 1

Gly Arg Val Cys Val Gln Pro Gly
1               5

```
<210> SEQ ID NO 2
<211> LENGTH: 8
<212> TYPE: PRT
<213> ORGANISM: Artificial Sequence
<220> FEATURE:
<223> OTHER INFORMATION: Zonulin Peptide Antagonist

<400> SEQUENCE: 2

Gly Arg Val Cys Val Gln Asp Gly
1               5

<210> SEQ ID NO 3
<211> LENGTH: 8
<212> TYPE: PRT
<213> ORGANISM: Artificial Sequence
<220> FEATURE:
<223> OTHER INFORMATION: Zonulin Peptide Antagonist

<400> SEQUENCE: 3

Gly Arg Val Leu Val Gln Pro Gly
1               5

<210> SEQ ID NO 4
<211> LENGTH: 8
<212> TYPE: PRT
<213> ORGANISM: Artificial Sequence
<220> FEATURE:
<223> OTHER INFORMATION: Zonulin Peptide Antagonist

<400> SEQUENCE: 4

Gly Arg Val Leu Val Gln Asp Gly
1               5

<210> SEQ ID NO 5
<211> LENGTH: 8
<212> TYPE: PRT
<213> ORGANISM: Artificial Sequence
<220> FEATURE:
<223> OTHER INFORMATION: Zonulin Peptide Antagonist

<400> SEQUENCE: 5

Gly Arg Leu Cys Val Gln Pro Gly
1               5

<210> SEQ ID NO 6
<211> LENGTH: 8
<212> TYPE: PRT
<213> ORGANISM: Artificial Sequence
<220> FEATURE:
<223> OTHER INFORMATION: Zonulin Peptide Antagonist

<400> SEQUENCE: 6

Gly Arg Leu Cys Val Gln Asp Gly
1               5

<210> SEQ ID NO 7
<211> LENGTH: 8
<212> TYPE: PRT
<213> ORGANISM: Artificial Sequence
<220> FEATURE:
<223> OTHER INFORMATION: Zonulin Peptide Antagonist

<400> SEQUENCE: 7

Gly Arg Leu Leu

```
<210> SEQ ID NO 8
<211> LENGTH: 8
<212> TYPE: PRT
<213> ORGANISM: Artificial Sequence
<220> FEATURE:
<223> OTHER INFORMATION: Zonulin Peptide Antagonist

<400> SEQUENCE: 8

Gly Arg Leu Leu Val Gln Asp Gly
1               5

<210> SEQ ID NO 9
<211> LENGTH: 8
<212> TYPE: PRT
<213> ORGANISM: Artificial Sequence
<220> FEATURE:
<223> OTHER INFORMATION: Zonulin Peptide Antagonist

<400> SEQUENCE: 9

Gly Arg Gly Cys Val Gln Pro Gly
1               5

<210> SEQ ID NO 10
<211> LENGTH: 8
<212> TYPE: PRT
<213> ORGANISM: Artificial Sequence
<220> FEATURE:
<223> OTHER INFORMATION: Zonulin Peptide Antagonist

<400> SEQUENCE: 10

Gly Arg Gly Cys Val Gln Asp Gly
1               5

<210> SEQ ID NO 11
<211> LENGTH: 8
<212> TYPE: PRT
<213> ORGANISM: Artificial Sequence
<220> FEATURE:
<223> OTHER INFORMATION: Zonulin Peptide Antagonist

<400> SEQUENCE: 11

Gly Arg Gly Leu Val Gln Pro Gly
1               5

<210> SEQ ID NO 12
<211> LENGTH: 8
<212> TYPE: PRT
<213> ORGANISM: Artificial Sequence
<220> FEATURE:
<223> OTHER INFORMATION: Zonulin Peptide Antagonist

<400> SEQUENCE: 12

Gly Arg Gly Leu Val Gln Asp Gly
1               5

<210> SEQ ID NO 13
<211> LENGTH: 8
<212> TYPE: PRT
<213> ORGANISM: Artificial Sequence
<220> FEATURE:
<223> OTHER INFORMATION: Zonulin Peptide Antagonist

<400> SEQUENCE: 13

Gly Gly Val Cys Val Gln Pro Gly
1               5

<210> SEQ ID NO 14
```

```
<211> LENGTH: 8
<212> TYPE: PRT
<213> ORGANISM: Artificial Sequence
<220> FEATURE:
<223> OTHER INFORMATION: Zonulin Peptide Antagonist

<400> SEQUENCE: 14

Gly Gly Val Cys Val Gln Asp Gly
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic Octapeptide

<400> SEQUENCE: 15

Gly Gly Val Leu Val Gln Pro Gly
1               5

<210> SEQ ID NO 16
<211> LENGTH: 8
<212> TYPE: PRT
<213> ORGANISM: Artificial Sequence
<220> FEATURE:
<223> OTHER INFORMATION: Zonulin Peptide Antagonist

<400> SEQUENCE: 16

Gly Gly Val Leu Val Gln Asp Gly
1               5

<210> SEQ ID NO 17
<211> LENGTH: 8
<212> TYPE: PRT
<213> ORGANISM: Artificial Sequence
<220> FEATURE:
<223> OTHER INFORMATION: Zonulin Peptide Antagonist

<400> SEQUENCE: 17

Gly Gly Leu Cys Val Gln Pro Gly
1               5

<210> SEQ ID NO 18
<211> LENGTH: 8
<212> TYPE: PRT
<213> ORGANISM: Artificial Sequence
<220> FEATURE:
<223> OTHER INFORMATION: Zonulin Peptide Antagonist

<400> SEQUENCE: 18

Gly Gly Leu Cys Val Gln Asp Gly
1               5

<210> SEQ ID NO 19
<211> LENGTH: 8
<212> TYPE: PRT
<213> ORGANISM: Artificial Sequence
<220> FEATURE:
<223> OTHER INFORMATION: Zonulin Peptide Antagonist

<400> SEQUENCE: 19

Gly Gly Leu Leu Val Gln Pro Gly
1               5

<210> SEQ ID NO 20
<211> LENGTH: 8
```

```
<212> TYPE: PRT
<213> ORGANISM: Artificial Sequence
<220> FEATURE:
<223> OTHER INFORMATION: Zonulin Peptide Antagonist

<400> SEQUENCE: 20

Gly Gly Leu Leu Val Gln Asp Gly
1               5

<210> SEQ ID NO 21
<211> LENGTH: 8
<212> TYPE: PRT
<213> ORGANISM: Artificial Sequence
<220> FEATURE:
<223> OTHER INFORMATION: Zonulin Peptide Antagonist

<400> SEQUENCE: 21

Gly Gly Gly Cys Val Gln Pro Gly
1               5

<210> SEQ ID NO 22
<211> LENGTH: 8
<212> TYPE: PRT
<213> ORGANISM: Artificial Sequence
<220> FEATURE:
<223> OTHER INFORMATION: Zonulin Peptide Antagonist

<400> SEQUENCE: 22

Gly Gly Gly Cys Val Gln Asp Gly
1               5

<210> SEQ ID NO 23
<211> LENGTH: 8
<212> TYPE: PRT
<213> ORGANISM: Artificial Sequence
<220> FEATURE:
<223> OTHER INFORMATION: Zonulin Peptide Antagonist

<400> SEQUENCE: 23

Gly Gly Gly Leu Val Gln Pro Gly
1               5

<210> SEQ ID NO 24
<211> LENGTH: 8
<212> TYPE: PRT
<213> ORGANISM: Artificial Sequence
<220> FEATURE:
<223> OTHER INFORMATION: Zonulin Peptide Antagonist

<400> SEQUENCE: 24

Gly Gly Gly Leu Val Gln Asp Gly
1               5

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence Synthetic
      Construct

<400> SEQUENCE: 25
tcatcacggc gcgccagg                                                 18

<210> SEQ ID NO 26
<211> LENGTH: 22
<212> TYPE: DNA
```

```
<213> ORGANISM: Artificial Sequence
<220> FEATURE:
<223> OTHER INFORMATION: Description of Artificial Sequence Synthetic
      Construct

<400> SEQUENCE: 26
ggaggtctag aatctgcccg at                                              22

<210> SEQ ID NO 27
<211> LENGTH: 18
<212> TYPE: PRT
<213> ORGANISM: Unknown
<220> FEATURE:
<223> OTHER INFORMATION: Rabbit
      intestine

<400> SEQUENCE: 27

Asn Gln Arg Pro Pro Pro Ala Gly Val Thr Ala Tyr Asp Tyr Leu Val
1               5                   10                  15

Ile Gln

<210> SEQ ID NO 28
<211> LENGTH: 20
<212> TYPE: PRT
<213> ORGANISM: Homo sapiens

<400> SEQUENCE: 28

Glu Val Gln Leu Val Glu Ser Gly Gly Gly Leu Val Gln Pro Gly Gly
1               5                   10                  15

Ser Leu Arg Leu
            20

<210> SEQ ID NO 29
<211> LENGTH: 9
<212> TYPE: PRT
<213> ORGANISM: Homo sapiens

<400> SEQUENCE: 29

Val Thr Phe Tyr Thr Asp Ala Val Ser
1               5

<210> SEQ ID NO 30
<211> LENGTH: 20
<212> TYPE: PRT
<213> ORGANISM: Homo sapiens
<220> FEATURE:
<221> NAME/KEY: misc_feature
<222> LOCATION: (16)..(16)
<223> OTHER INFORMATION: Xaa can be any naturally occurring amino acid

<400> SEQUENCE: 30

Met Leu Gln Leu Ala Glu Ser Gly Gly Val Leu Val Gln Pro Gly Xaa
1               5                   10                  15

Ser Asn Arg Leu
            20

<210> SEQ ID NO 31
<211> LENGTH: 11
<212> TYPE: PRT
<213> ORGANISM: Homo sapiens
<220> FEATURE:
<221> NAME/KEY: misc_feature
<222> LOCATION: (10)..(10)
<223> OTHER INFORMATION: Xaa can be any naturally occurring amino acid

<400> SEQUENCE: 31
```

```
Glu Val Gln Leu Val Glu Ser Gly Gly Xaa Leu
1               5                   10
```

```
<210> SEQ ID NO 32
<211> LENGTH: 11
<212> TYPE: PRT
<213> ORGANISM: Homo sapiens
<220> FEATURE:
<221> NAME/KEY: misc_feature
<222> LOCATION: (1)..(2)
<223> OTHER INFORMATION: Xaa can be any naturally occurring amino acid

<400> SEQUENCE: 32

Xaa Xaa Asp Gly Thr Gly Leu Val Gly Asp Leu
1               5                   10

<210> SEQ ID NO 33
<211> LENGTH: 13
<212> TYPE: PRT
<213> ORGANISM: Homo sapiens

<400> SEQUENCE: 33

Leu Ser Glu Val Thr Ala Val Pro Ser Leu Asn Gly Gly
1               5                   10

<210> SEQ ID NO 34
<211> LENGTH: 8
<212> TYPE: PRT
<213> ORGANISM: Artificial sequence
<220> FEATURE:
<223> OTHER INFORMATION: Synthetic octapeptide

<400> SEQUENCE: 34

Val Gly Val Leu Gly Arg Pro Gly
1               5

<210> SEQ ID NO 35
<211> LENGTH: 8
<212> TYPE: PRT
<213> ORGANISM: Artificial Sequence
<220> FEATURE:
<223> OTHER INFORMATION: Zonulin Peptide Antagonist

<400> SEQUENCE: 35

Val Asn Gly Phe Gly Arg Ile Gly
1               5

<210> SEQ ID NO 36
<211> LENGTH: 22
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 36

Xaa Gly Lys Val Lys Val Gly Val Asn Gly Phe Gly Arg Ile Gly Arg
1               5                   10                  15

Ile Gly Arg Leu Val Ile
            20

<210> SEQ ID NO 37
<211> LENGTH: 20
<212> TYPE: PRT
<213> ORGANISM: Homo sapiens
```

```
-continued

<400> SEQUENCE: 37

Glu Val Gln Leu Val Glu Ser Gly Gly Gly Leu Val Gln Pro Gly Arg
1               5                   10                  15

Ser Leu Arg Leu
            20

<210> SEQ ID NO 38
<211> LENGTH: 14
<212> TYPE: PRT
<213> ORGANISM: Unknown
<220> FEATURE:
<223> OTHER INFORMATION: Zonulin Occludes Toxin

<400> SEQUENCE: 38

Phe Cys Ile Gly Arg Leu Cys Val Gln Asp Gly Phe Val Thr
1               5                   10

<210> SEQ ID NO 39
<211> LENGTH: 23
<212> TYPE: DNA
<213> ORGANISM: Artificial sequence
<220> FEATURE:
<223> OTHER INFORMATION: Synthetic Construct

<400> SEQUENCE: 39
cgggatcccg tatgagtatc ttt                                              23

<210> SEQ ID NO 40
<211> LENGTH: 24
<212> TYPE: DNA
<213> ORGANISM: Artificial Sequence
<220> FEATURE:
<223> OTHER INFORMATION: Synthetic Construct

<400> SEQUENCE: 40
cccaagcttg ggtcaaaata tact                                             24
```